United States Patent
Dakin et al.

(10) Patent No.: US 7,723,337 B2
(45) Date of Patent: May 25, 2010

(54) 3-CINNOLINECARBOXAMIDE DERIVATIVES AND THEIR USE FOR TREATING CANCER

(75) Inventors: Leslie Dakin, Waltham, MA (US); Claude Afona Ogoe, Waltham, MA (US); David Scott, Waltham, MA (US); XiaoLan Zheng, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/210,588

(22) Filed: Sep. 15, 2008

(65) Prior Publication Data

US 2009/0012084 A1    Jan. 8, 2009

Related U.S. Application Data

(63) Continuation of application No. PCT/GB2008/000256, filed on Jan. 24, 2008.

(60) Provisional application No. 60/886,585, filed on Jan. 25, 2007, provisional application No. 60/951,576, filed on Jul. 24, 2007.

(51) Int. Cl.
  A01N 43/58    (2006.01)
  A01N 43/60    (2006.01)
  A61K 31/50    (2006.01)
  A61K 31/495   (2006.01)
  A61K 31/4965  (2006.01)
  C07D 237/26   (2006.01)
  C07D 487/00   (2006.01)
  C07D 237/28   (2006.01)
  C07D 241/04   (2006.01)
  C07D 295/00   (2006.01)

(52) U.S. Cl. ............... 514/248; 514/255.03; 544/235; 544/380

(58) Field of Classification Search ............ 514/248, 514/255.03; 544/233, 380
See application file for complete search history.

(56) References Cited

U.S. PATENT DOCUMENTS

| | | | |
|---|---|---|---|
| 4,806,550 | A | 2/1989 | Ife et al. |
| 5,026,711 | A | 6/1991 | Mendes et al. |
| 5,215,999 | A | 6/1993 | Uchida et al. |
| 7,037,925 | B2 | 5/2006 | Larsson |
| 2006/0264439 | A1 | 11/2006 | Bearss et al. |
| 2007/0191426 | A1 | 8/2007 | Edlin |

FOREIGN PATENT DOCUMENTS

| | | | |
|---|---|---|---|
| WO | 96/40681 | A1 | 12/1996 |
| WO | 97/22596 | A1 | 6/1997 |
| WO | 97/30035 | A1 | 8/1997 |
| WO | 97/32856 | A1 | 9/1997 |
| WO | 98/13354 | A1 | 4/1998 |
| WO | 99/02166 | A1 | 1/1999 |
| WO | 00/40529 | A1 | 7/2000 |
| WO | 00/41669 | A2 | 7/2000 |
| WO | 01/92224 | A1 | 12/2001 |
| WO | 02/04434 | A1 | 1/2002 |
| WO | 02/08213 | A1 | 1/2002 |
| WO | 2006/067445 | A2 | 6/2006 |
| WO | 2006/124996 | A2 | 11/2006 |
| WO | WO 2006/124996 | * | 11/2006 |
| WO | 2007/045861 | A1 | 4/2007 |
| WO | 2007/119046 | A1 | 10/2007 |
| WO | 2008/056148 | A1 | 5/2008 |

OTHER PUBLICATIONS

Pixley, Fiona J. et al., CSF-1 Regulation of the wandering macrophage: complexity in action, TRENDS in Cell Biology, Nov. 2004, 628-638, vol. 14, No. 11.
Sapi, Eva, The Role of CSF-1 in Normal Physiology of Mammary Gland and Breast Cancer: An Update, Experimental Biology and Medicine, 2004, pp. 1-11, vol. 229.
Sherr, Charles J., The fms oncogne, Biochimica et Biophysica Acta, 1988, pp. 225-243, vol. 948.
Teitelbaum, et al., Bone Resorption by Osteoclasts, Science, 2000, pp. 1504-1508, vol. 289.

* cited by examiner

Primary Examiner—San-ming Hui
Assistant Examiner—Paul Zarek

(57) ABSTRACT

The invention relates to chemical compounds of formula (I):

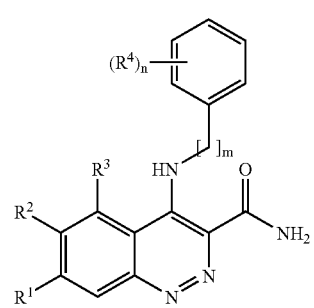

or pharmaceutically acceptable salts thereof which possess CSF-1R kinase inhibitory activity and are accordingly useful for their anti-cancer activity and thus in methods of treatment of the human or animal body. The invention also relates to processes for the manufacture of said chemical compounds, to pharmaceutical compositions containing them and to their use in the manufacture of medicaments of use in the production of an anti-cancer effect in a warm-blooded animal such as man.

11 Claims, No Drawings

3-CINNOLINECARBOXAMIDE DERIVATIVES AND THEIR USE FOR TREATING CANCER

This is a Continuation Application of International Application No. PCT/GB2005/000256 (filed 24 Jan., 2008) which claims priority to U.S. Provisional Application No. 60/886,585 filed on 25 Jan. 2007 and U.S. Provisional Application No. 60/951,576 filed on 24 Jul. 2007.

The invention relates to chemical compounds, or pharmaceutically acceptable salts thereof, which possess colony stimulating factor 1 receptor (CSF-1R) kinase inhibitory activity and are accordingly useful for their anti-cancer activity and thus in methods of treatment of the human or animal body. The invention also relates to processes for the manufacture of said chemical compounds, to pharmaceutical compositions containing them and to their use in the manufacture of medicaments of use in the production of an anti-cancer effect in a warm-blooded animal such as man.

Receptor tyrosine kinases (RTK's) are a sub-family of protein kinases that play a critical role in cell signalling and are involved in a variety of cancer related processes including cell proliferation, survival, angiogenesis, invasion and metastasis. There are believed to be at least 96 different RTK's including CSF-1R.

CSF-1R or c-fms was originally identified as the oncogene v-fms from the feline sarcoma virus. CSF-1R is a member of the class III RTK's along with c-Kit, fms-related tyrosine kinase 3 (Flt3) and Platelet-derived growth factor receptor α and β (PDGFRα and PDGFRβ). All of these kinases have been implicated in the process of tumorigenesis. CSF-1R is normally expressed as an immature 130 kDa transmembrane protein and ultimately results in a mature 145-160 kDa cell surface N-linked glycosylated protein. Macrophage colony stimulating factor (M-CSF or CSF-1), the ligand for CSF-1R, binds to the receptor resulting in dimerization, auto-phosphorylation of the receptor and subsequent activation of downstream signal transduction cascades (C. J. Sherr, Biochim Biophys Acta, 1988, 948: 225-243).

CSF-1R is normally expressed in myeloid cells of the mononuclear phagocytic lineage and their bone-marrow progenitors as well as the epithelial cells of the ducts and alveoli in the lactating, but not normal resting, breast tissue. CSF-1R activation stimulates the proliferation, survival, motility and differentiation of cells of the monocyte/macrophage lineage. The mature macrophage plays a key role in normal tissue development and immune defense (F. L. Pixley and E. R. Stanley, Trends in Cell Biology, 2004, 14(11): 628-638). For example, osteoblasts secrete CSF-1 and activate the receptor on osteoclastic progenitors resulting in differentiation into mature osteoclasts (S. L. Teitelbaum, Science, 2000, 289: 1504-1508). The CSF-1R axis plays an important role in placental development, embryonic implantation, mammary gland ductal and lobuloalveolar development and lactation (E. Sapi, Exp Biol Med, 2004, 229:1-11).

Transfection of CSF-1R with or without CSF-1 induces transformation and in vivo tumorigenicity of NIH3T3 (Rat2 and ovarian granulosa cells. Autocrine and/or paracrine signaling mechanisms have been implicated in the activation of CSF-1R in the tumour epithelium and tumour associated macrophage. Aberrant expression and activation of CSF-1R and/or its ligand have been found in human myeloid leukaemia, prostate, breast, ovarian, endometrial and a variety of other cancers. A number of studies have demonstrated that the overexpression of CSF-1R is associated with poor prognosis in several of these cancers. In addition, the CSF-1/CSF-1R axis plays a key role in the regulation of tumour-associated macrophage, which have been postulated to play a significant role in tumour angiogenesis, invasion and progression (E. Sapi, Exp Biol Med, 2004, 229:1-11).

In WO 2006/124996 Supergen Inc discloses certain inhibiters of Polo-Like Kinase-1; in WO/2007045861 Aston et al., and Glaxo Group Limited disclose certain inhibitor of phosphodiesterase type IV, and in WO2006/067445 AstraZeneca discloses certain inhibitors of CSF-1R. The present inventors have found that a novel class of cinnolines are inhibitors of CSF-1R and this forms the basis of the present invention.

Accordingly, the present invention provides a compound of formula (I):

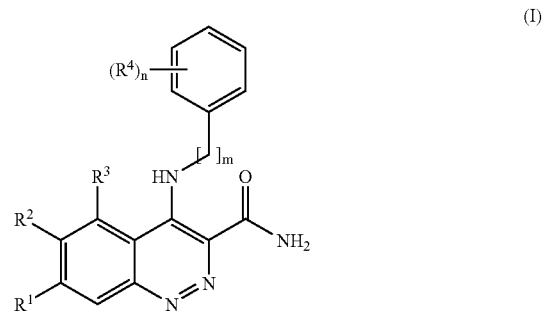

(I)

wherein:

$R^1$ and $R^2$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^5$; and wherein if said heterocyclyl contains an —NH— moiety that nitrogen may be optionally substituted by a group selected from $R^6$;

$R^3$ is hydrogen or halo;

m is 0 or 1;

$R^4$ is selected from halo, nitro, cyano, hydroxy, trifluoromethoxy, trifluoromethyl, amino, carboxy, carbamoyl, mercapto, sulphamoyl, $C_{1-4}$alkyl, $C_{2-4}$alkenyl, $C_{2-4}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or wherein if two $R^4$ groups are on adjacent carbons, they may optionally form a carbocyclic ring or a heterocyclic ring; wherein said carbocyclic ring or heterocyclic ring may be optionally substituted on carbon by one or more $R^7$; and wherein if said heterocyclic ring contains an —NH— moiety that nitrogen may be optionally substituted by a group selected from $R^8$;

n is 0-5; wherein the values of $R^4$ are the same or different;

$R^5$ is selected from halo, nitro, cyano, hydroxy, trifluoromethoxy, amino, carboxy, carbamoyl, mercapto, sulphamoyl, $C_{1-16}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, N—($C_{1-6}$alkyl)-N—($C_{1-6}$alkoxy) amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^9$— or heterocyclyl-$R^{10}$—; wherein $R^5$ may be optionally substituted on carbon by one or more $R^{11}$; and wherein if said heterocyclyl contains an —NH-moiety that nitrogen may be optionally substituted by a group selected from $R^{12}$;

$R^6$ and $R^{12}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^6$ and $R^{12}$ independently of each other may be optionally substituted on carbon by one or more $R^{13}$;

$R^{13}$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, N—($C_{1-6}$alkyl)-N—($C_{1-6}$alkoxy) amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^{14}$— or heterocyclyl-$R^{15}$—; wherein $R^{13}$ may be optionally substituted on carbon by one or more $R^{16}$; and wherein if said heterocyclyl contains an —NH— moiety that nitrogen may be optionally substituted by a group selected from $R^{17}$;

$R^9$, $R^{10}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_s$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-6}$alkyl and s is 0-2;

$R^8$ and $R^{17}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

$R^7$, $R^{11}$ and $R^{16}$ are independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

In some embodiments, the invention relates to a compound of formula (I):

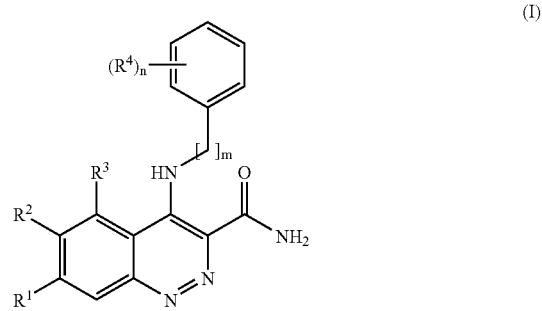

wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$carbamoyl, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^5$; and wherein if said heterocyclyl contains an —NH— moiety that nitrogen may be optionally substituted by a group selected from $R^6$;

$R^3$ is hydrogen or halo;

m is 0 or 1;

$R^4$ is selected from halo, nitro, cyano, hydroxy, trifluoromethoxy, trifluoromethyl, amino, carboxy, carbamoyl, mercapto, sulphamoyl, $C_{1-4}$alkyl, $C_{2-4}$alkenyl, $C_{2-4}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or wherein if two $R^4$ groups are on adjacent carbons, they may optionally form a carbocyclic ring or a heterocyclic ring; wherein said carbocyclic ring or heterocyclic ring may be optionally substituted on carbon by one or more $R^7$; and wherein if said heterocyclic ring contains an —NH— moiety that nitrogen may be optionally substituted by a group selected from $R^8$;

n is 0-5; wherein the values of $R^4$ are the same or different;

$R^5$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, N—($C_{1-6}$alkyl)-N—($C_{1-6}$alkoxy) amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^9$— or heterocyclyl-$R^{10}$—; wherein $R^5$ may be optionally substituted on carbon by one or more $R^{11}$; and wherein if said heterocyclyl contains an —NH-moiety that nitrogen may be optionally substituted by a group selected from $R^{12}$;

$R^6$ and $R^{12}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-16}$alkyl)carbamoyl, N,N—($C_{1-6}$alkyl)carbamoyl, benzyl, benzyloxycarbonyl, benzoyl and phenylsulphonyl; wherein $R^6$ and $R^{12}$ independently of each other may be optionally substituted on carbon by one or more $R^{13}$;

$R^{13}$ is selected from halo, nitro, cyano, hydroxy, trifluoromethoxy, amino, carboxy, carbamoyl, mercapto, sulphamoyl, $C_{1-16}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^{14}$— or heterocyclyl-$R^{15}$—; wherein $R^{13}$ may be optionally substituted on carbon by one or more $R^{16}$; and wherein if said heterocyclyl contains an —NH— moiety that nitrogen may be optionally substituted by a group selected from $R^{17}$;

$R^9$, $R^{10}$, $R^{14}$ and $R^{15}$ are independently selected from a direct bond, —O—, —N($R^{11}$)—, —C(O)—, —N($R^{19}$)C(O)—, —C(O)N($R^{20}$)—, —S(O)$_s$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-6}$alkyl and s is 0-2;

$R^8$ and $R^{17}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-16}$alkyl)carbamoyl, N,N—($C_{1-6}$alkyl)carbamoyl, benzyl, benzyloxycarbonyl, benzoyl and phenylsulphonyl;

$R^7$, $R^{11}$ and $R^{16}$ are independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

In some embodiments, the invention relates to a compound of formula (I) having formula (IA):

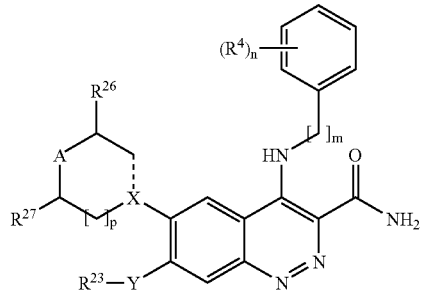

formula (IA)

or a pharmaceutically acceptable salt thereof, wherein:
--- is selected from a single and double bond;
if --- is a single bond, then X is selected from CR$^{24}$ and N;
if --- is a double bond, then X is C;
Y is selected from O and S;
A is selected from O, S, NR$^{25}$, and CR$^{28}$R$^{29}$;
p is 0-2;
m is 0 or 1;
$R^4$ is independently selected from halo, nitro, cyano, hydroxy, trifluoromethoxy, trifluoromethyl, amino, carboxy, carbamoyl, mercapto, sulphamoyl, $C_{1-4}$alkyl, $C_{2-4}$alkenyl, $C_{2-4}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or wherein if two $R^4$ groups are on adjacent carbons, they may optionally form a carbocyclic ring or a heterocyclic ring; wherein said carbocyclic ring or heterocyclic ring may be optionally substituted on carbon by one or more $R^7$; and wherein if said heterocyclic ring contains an —NH— moiety that nitrogen may be optionally substituted by a group selected from $R^8$;

n is 0-5; wherein the values of $R^4$ are the same or different;

$R^7$ may be independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

$R^8$ may be selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

$R^{23}$ is selected from H, and $C_{1-6}$alkyl wherein $C_{1-6}$alkyl is optionally substituted with $C_{1-6}$alkoxy;

$R^{24}$, $R^{26}$, $R^{27}$, $R^{28}$ are each independently selected from hydrogen and $C_{1-6}$alkyl;

$R^{25}$ may be selected from hydrogen, $C_{1-6}$alkyl and $C_{1-6}$alkanoyl, wherein $C_{1-6}$alkyl and $C_{1-6}$alkanoyl may be optionally substituted on carbon by one or more $R^{30}$;

or $R^{25}$ and $R^{27}$ together with the atom they are attached may optionally form a heterocyclic ring; wherein said heterocyclic ring may be optionally substituted on carbon by one or more $R^{35}$; and wherein if said heterocyclic ring contains an —NH— moiety that nitrogen may be optionally substituted by a group selected from $R^{36}$;

$R^{29}$ may be selected from hydrogen and amino, wherein amino may be optionally substituted with one or more $C_{1-6}$alkyl;

$R^{30}$ may be selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl; and $R^{35}$ may be independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

$R^{36}$ may be selected from $C_{1-6}$alkyl, $C_{1-6}$alkanoyl, $C_{1-6}$alkylsulphonyl, $C_{1-6}$alkoxycarbonyl, carbamoyl, N—$(C_{1-6}$alkyl)carbamoyl, N,N—$(C_{1-6}$alkyl)carbamoyl, benzyl, benzyloxycarbonyl, benzoyl and phenylsulphonyl.

In some embodiments, the invention relates to a compound of formula (I) having formula (IB):

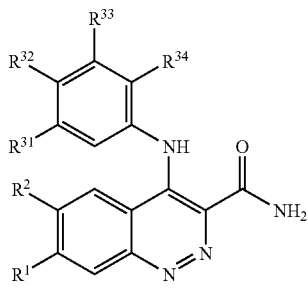

formula (IB)

or a pharmaceutically acceptable salt thereof, wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$-amino, N—$(C_{1-6}$alkyl)-N—$(C_{1-6}$alkoxy)amino, $C_{1-6}$alkanoylamino, N—$(C_{1-6}$alkyl)carbamoyl, N,N—$(C_{1-6}$alkyl)$_2$-carbamoyl, $C_{1-6}$alkoxycarbonyl, N—$(C_{1-6}$alkyl)sulphamoyl, N,N—$(C_{1-6}$alkyl)$_2$sulphamoyl, $C_{1-16}$alkylsulphonylamino, carbocyclyl or heterocyclyl; wherein $R^1$ and $R^2$ independently of each other may be optionally substituted on carbon by one or more $R^5$; and wherein if said heterocyclyl contains an —NH— moiety that nitrogen may be optionally substituted by a group selected from $R^6$;

$R^5$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, N—$(C_{1-6}$alkyl)-N—$(C_{1-6}$alkoxy)amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—$(C_{1-6}$alkyl)sulphamoyl, N,N—$(C_{1-6}$alkyl)$_2$sulphamoyl, $C_{1-6}$alkylsulphonylamino, carbocyclyl-$R^9$— or heterocyclyl-$R^{10}$—; wherein $R^5$ may be optionally substituted on carbon by one or more $R^{11}$; and wherein if said heterocyclyl contains an —NH-moiety that nitrogen may be optionally substituted by a group selected from $R^{12}$;

$R^6$ and $R^{12}$ are independently selected from $C_{1-6}$alkyl, $C_{1-6}$alkanoyl, $C_{1-6}$alkylsulphonyl, $C_{1-6}$alkoxycarbonyl, carbamoyl, N—$(C_{1-6}$alkyl)carbamoyl, N,N—$(C_{1-6}$alkyl)carbamoyl, benzyl, benzyloxycarbonyl, benzoyl and phenylsulphonyl; wherein $R^6$ and $R^{12}$ independently of each other may be optionally substituted on carbon by one or more $R^{13}$;

$R^{13}$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, N—$(C_{1-6}$alkyl)-N—$(C_{1-6}$alkoxy)amino, $C_{1-6}$alkanoylamino, N—$(C_{1-6}$alkyl)carbamoyl, N,N—$(C_{1-6}$alkyl)$_2$-carbamoyl, $C_{1-6}$alkylS(O)$_a$ wherein a is 0 to 2, $C_{1-6}$alkoxycarbonyl, $C_{1-6}$alkoxycarbonylamino, N—$(C_{1-6}$alkyl)sulphamoyl, N,N—$(C_{1-6}$alkyl)$_2$sulphamoyl, $C_{1-6}$alkylsulphonylamino, carbocyclyl-$R^{14}$— or heterocyclyl-$R^{15}$—; wherein $R^{13}$ may be optionally substituted on carbon by one or more $R^{16}$; and wherein if said heterocyclyl contains an —NH— moiety that nitrogen may be optionally substituted by a group selected from $R^{17}$;

$R^9$, $R^{10}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_s$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-6}$alkyl and s is 0-2;

$R^{17}$ are independently selected from $C_{1-6}$alkyl, $C_{1-6}$alkanoyl, $C_{1-6}$alkylsulphonyl, $C_{1-6}$alkoxycarbonyl, carbamoyl, N—$(C_{1-6}$alkyl)carbamoyl, N,N—$(C_{1-6}$alkyl)carbamoyl, benzyl, benzyloxycarbonyl, benzoyl and phenylsulphonyl;

$R^{11}$ and $R^{16}$ are independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{31}$, $R^{32}$, $R^{33}$, and $R^{34}$ are each independently selected from hydrogen, halo, and $C_{1-4}$alkyl.

In some embodiments, the invention relates to a compound of formula (I) having formula (IC):

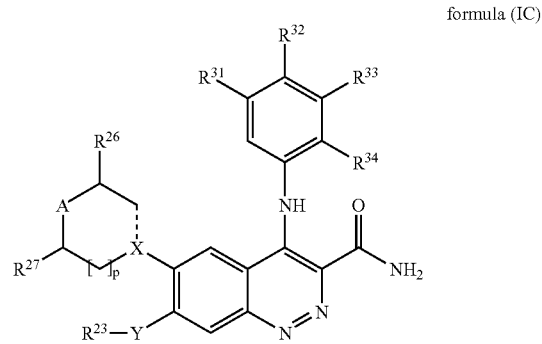

formula (IC)

or a pharmaceutically acceptable salt thereof, wherein:
--- is selected from a single and double bond;
if --- is a single bond, then X is selected from CR$^{24}$ and N;
if --- is a double bond, then X is C;
Y is selected from O and S;

A is selected from O, S, $NR^{25}$, and $CR^{28}R^{29}$;

p is 0-2;

$R^{23}$ is $C_{1-6}$alkyl;

$R^{24}$, $R^{26}$, $R^{27}$, $R^{28}$ are each independently selected from hydrogen and $C_{1-6}$alkyl;

$R^{25}$ may be selected from hydrogen, $C_{1-6}$alkyl and $C_{1-6}$alkanoyl wherein $C_{1-6}$alkyl and $C_{1-6}$alkanoyl may be optionally substituted on carbon by one or more $R^{30}$;

$R^{29}$ may be selected from hydrogen and amino optionally substituted with one or more $C_{1-6}$alkyl;

$R^{30}$ may be selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, and N-methyl-N-ethylsulphamoyl;

$R^{31}$ is selected from hydrogen and $C_{1-4}$alkyl;

$R^{32}$ is selected from hydrogen, halo, and $C_{1-4}$alkyl;

$R^{33}$ is selected from hydrogen and halo; and $R^{34}$ is selected from halo.

In some embodiments, the invention relates to a compound of formula (I) having formula (ID):

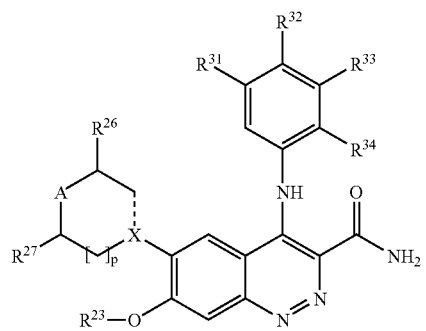

formula (ID)

or a pharmaceutically acceptable salt thereof, wherein:

--- is selected from a single and double bond;

if --- is a single bond, then X is selected from CH and N;

if --- is a double bond, then X is C;

A is selected from O, $NR^{25}$, and $CHR^{29}$;

p is 0-2;

$R^{23}$ is selected from methyl and ethyl;

$R^{25}$ is selected from hydrogen, methyl, ethyl, isopropyl, tert-butyl, 1-methoxy-2-ethyl, 1-hydroxy-2-ethyl, 1,1,1-trifluoro-2-ethyl, 2-hydroxy-1-propionyl, and mesyl;

$R^{26}$ and $R^{27}$, are each independently selected from hydrogen and methyl;

$R^{29}$ may be dimethylamino;

$R^{31}$ is selected from hydrogen and methyl;

$R^{32}$ is selected from hydrogen, fluoro, and methyl;

$R^{33}$ is selected from hydrogen and chloro; and $R^{34}$ is selected from fluoro and chloro.

In some embodiments, the invention relates to a compound of formula (I) having formula (IE):

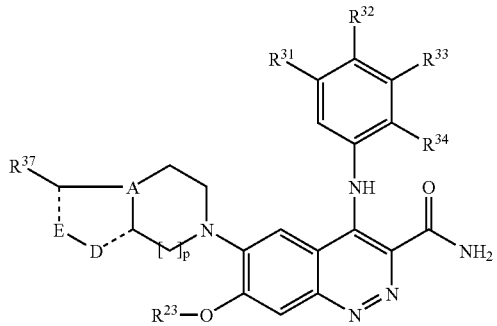

formula (IE)

or a pharmaceutically acceptable salt thereof, wherein:

--- is selected from a single and double bond;

A is selected from N, and CH;

D is selected from N, NH, CH, and $CH_2$;

E is selected from N, NH, CH, and $CH_2$;

p is 0-1;

$R^{23}$ is selected from $C_{1-6}$alkyl;

$R^{31}$ is selected from hydrogen and $C_{1-4}$alkyl;

$R^{32}$ is selected from hydrogen, halo, and $C_{1-4}$alkyl;

$R^{33}$ is selected from hydrogen and halo; and $R^{34}$ is halo; and $R^{37}$ is selected from H and OH.

In this specification the term "alkyl" includes both straight and branched chain alkyl groups. References to individual alkyl groups such as "propyl" are specific for the straight chain version only and references to individual branched chain alkyl groups such as 'isopropyl' are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl$C_{1-6}$alkyl" includes phenyl$C_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form the S-oxides. Examples and suitable values of the term "heterocyclyl" are morpholino, piperidyl, pyridyl, pyranyl, pyrrolyl, pyrazolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. A particular example of the term "heterocyclyl" is pyrazolyl. In one aspect of the invention a "heterocyclyl" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked, a —CH$_2$— group can optionally be replaced by a —C(O)— and a ring sulphur atom may be optionally oxidised to form the S-oxides.

A "carbocyclyl" is a saturated, partially saturated or unsaturated, mono or bicyclic carbon ring that contains 3-12 atoms; wherein a —CH$_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. A particular example of "carbocyclyl" is phenyl.

"If two R$^4$ groups are on adjacent carbons, they may optionally form a carbocyclic ring or a heterocyclic ring". Said "carbocyclic ring" or a "heterocyclic ring" is therefore fused to the phenyl ring of formula (I).

A "carbocyclic ring" is a partially saturated or totally unsaturated, monocyclic ring that contains 3-8 carbon atoms of which two are shared with the phenyl ring in formula (I); wherein a —CH$_2$— group can optionally be replaced by a —C(O)—. Suitable examples of a "carbocyclic ring" fused to the phenyl ring in formula (I) include indanyl (carbocyclic ring is a partially saturated 5 membered ring) and naphthyl (carbocyclic ring is a totally unsaturated 6 membered ring).

A "heterocyclic ring" is a partially saturated or totally unsaturated, monocyclic ring containing 4-8 atoms of which at least one atom is chosen from nitrogen, sulphur or oxygen and two atoms are carbon atoms shared with the phenyl ring in formula (I); wherein a —CH$_2$— group can optionally be replaced by a —C(O)— and a ring sulphur atom may be optionally oxidised to form the S-oxides. Suitable examples of a "heterocyclic ring" fused to the phenyl ring in formula (I) include indolinyl (heterocyclic ring is a partially saturated 5 membered ring containing one nitrogen atom) and quinoxalinyl (heterocyclic ring is a totally unsaturated 6 membered ring containing two nitrogen atoms).

An example of "C$_{1-6}$alkanoyloxy" is acetoxy. Examples of "C$_{1-6}$alkoxycarbonyl" include methoxycarbonyl, ethoxycarbonyl, n- and t-butoxycarbonyl. Examples of "C$_{1-6}$alkoxy" include methoxy, ethoxy and propoxy. Examples of "C$_{1-6}$alkanoylamino" include formamido, acetamido and propionylamino. Examples of "C$_{1-6}$alkylS(O)$_a$ wherein a is 0 to 2" include methylthio, ethylthio, methylsulphinyl, ethylsulphinyl, mesyl and ethylsulphonyl. Examples of "C$_{1-6}$alkanoyl" include propionyl and acetyl. Examples of "N—(C$_{1-6}$alkyl)amino" include methylamino and ethylamino. Examples of "N,N—(C$_{1-6}$alkyl)$_2$-amino" include di-N-methylamino, di-(N-ethyl)amino and N-ethyl-N-methylamino. Examples of "C$_{2-6}$alkenyl" are vinyl, allyl and 1-propenyl. Examples of "C$_{2-6}$alkynyl" are ethynyl, 1-propynyl and 2-propynyl. Examples of "N—(C$_{1-6}$alkyl)sulphamoyl" are N-(methyl)sulphamoyl and N-(ethyl)sulphamoyl. Examples of "N—(C$_{1-6}$alkyl)$_2$sulphamoyl" are N,N-(dimethyl)sulphamoyl and N-(methyl)-N-(ethyl)sulphamoyl. Examples of "N—(C$_{1-6}$alkyl)carbamoyl" are N—(C$_{1-4}$alkyl)carbamoyl, methylaminocarbonyl and ethylaminocarbonyl. Examples of "N,N—(C$_{1-6}$alkyl)$_2$-carbamoyl" are N,N—(C$_{1-14}$alkyl)$_2$-carbamoyl, dimethylaminocarbonyl and methylethylaminocarbonyl. Examples of "C$_{1-6}$alkylsulphonyl" are mesyl, ethylsulphonyl and isopropylsulphonyl. Examples of "C$_{1-6}$alkylsulphonylamino" are mesylamino, ethylsulphonylamino and isopropylsulphonylamino. Examples of "C$_{1-6}$alkoxycarbonylamino" are methoxycarbonylamino and t-butoxycarbonylamino. Examples of "C$_{1-6}$alkoxycarbonylamino" include methoxycarbonylamino and t-butoxycarbonylamino.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Some compounds of the formula (I) may have chiral centres and/or geometric isomeric centres (E- and Z-isomers), and it is to be understood that the invention encompasses all such optical, diastereoisomers and geometric isomers that possess CSF-1R kinase inhibitory activity. The invention further relates to any and all tautomeric forms of the compounds of the formula (I) that possess CSF-1R kinase inhibitory activity.

It is also to be understood that certain compounds of the formula (I) can exist in solvated as well as unsolvated forms such as, for example, hydrated forms. It is to be understood that the invention encompasses all such solvated forms which possess CSF-1R kinase inhibitory activity.

Particular values of variable groups are as follows. Such values may be used where appropriate with any of the definitions, claims or embodiments defined hereinbefore or hereinafter.

R$^1$ and R$^2$ are independently selected from C$_{1-6}$alkoxy or heterocyclyl; wherein R$^1$ and R$^2$ independently of each other may be optionally substituted on carbon by one or more R$^5$; and wherein if said heterocyclyl contains an —NH— moiety that nitrogen may be optionally substituted by a group selected from R$^6$; wherein R$^5$ is C$_{1-6}$alkoxy; and R$^6$ is C$_{1-6}$alkyl.

R$^1$ and R$^2$ are independently selected from C$_{1-6}$alkoxy or heterocyclyl; wherein if said heterocyclyl contains an —NH— moiety that nitrogen may be optionally substituted by a group selected from R$^6$; wherein R$^6$ is selected from C$_{1-6}$alkyl.

R$^1$ and R$^2$ are independently selected from C$_{1-6}$alkoxy or piperazinyl; wherein R$^1$ and R$^2$ independently of each other may be optionally substituted on carbon by one or more R$^5$; and wherein if said heterocyclyl contains an —NH— moiety that nitrogen may be optionally substituted by a group selected from R$^6$; wherein R$^5$ is C$_{1-6}$alkoxy; and R$^6$ is C$_{1-6}$alkyl.

R$^1$ and R$^2$ are independently selected from C$_{1-6}$alkoxy or piperazinyl; wherein said piperazinyl may be optionally substituted on nitrogen by a group selected from R$^6$; wherein R$^6$ is selected from C$_{1-6}$alkyl.

R$^1$ and R$^2$ are independently selected from methoxy, ethoxy or piperazin-1-yl; wherein R$^1$ and R$^2$ independently of each other may be optionally substituted on carbon by one or more R$^5$; and wherein if said heterocyclyl contains an —NH— moiety that nitrogen may be optionally substituted by a group selected from R$^6$; wherein R$^5$ is methoxy; and R$^6$ is methyl, ethyl, isopropyl or t-butyl.

R$^1$ and R$^2$ are independently selected from methoxy, ethoxy or piperazinyl; wherein said piperazinyl may be optionally substituted on nitrogen by a group selected from $R^6$; wherein $R^6$ is selected from methyl, ethyl or isopropyl.

$R^1$ and $R^2$ are independently selected from 2-methoxyethoxy, ethoxy, methoxy, 4-ethylpiperazin-1-yl, 4-isopropylpiperazin-1-yl, 4-methylpiperazin-1-yl or 4-tert-butylpiperazin-1-yl.

$R^1$ and $R^2$ are independently selected from methoxy, ethoxy, 1-methylpiperazin-4-yl, 1-ethylpiperazin-4-yl or 1-isopropylpiperazin-4-yl.

$R^1$ and $R^2$ are both methoxy or $R^1$ is ethoxy and $R^2$ is selected from 1-methylpiperazin-4-yl, 1-ethylpiperazin-4-yl or 1-isopropylpiperazin-4-yl.

$R^1$ and $R^2$ are both methoxy.

$R^1$ is ethoxy and $R^2$ is selected from 1-methylpiperazin-4-yl, 1-ethylpiperazin-4-yl or 1-isopropylpiperazin-4-yl.

$R^1$ is 2-methoxyethoxy, ethoxy or methoxy.

$R^2$ is 4-ethylpiperazin-1-yl, 4-isopropylpiperazin-1-yl, 4-methylpiperazin-1-yl, 4-tert-butylpiperazin-1-yl or methoxy.

$R^1$ is 2-methoxyethoxy, ethoxy or methoxy and $R^2$ is 4-ethylpiperazin-1-yl, 4-isopropylpiperazin-1-yl, 4-methylpiperazin-1-yl, 4-tert-butylpiperazin-1-yl or methoxy.

$R^3$ is hydrogen.

m is 0.

m is 1.

$R^4$ is selected from halo or methyl.

$R^4$ is selected from fluoro, chloro or methyl.

n is 2; wherein the values of $R^4$ are the same or different.

$R^4$, n and the phenyl to which they are attached form 2,3-dichlorophenyl, 2,4-difluorophenyl, 2-fluoro-4-methyl-phenyl, 2-fluoro-5-methyl-phenyl or 3-chloro-2-fluoro-phenyl.

Therefore in a further aspect of the invention there is provided a compound of formula (I) (as depicted above) wherein:

$R^1$ and $R^2$ are independently selected from $C_{1-6}$alkoxy or heterocyclyl; wherein $R^1$ and $R^2$ independently of each other may be optionally substituted on carbon by one or more $R^5$; and wherein if said heterocyclyl contains an —NH— moiety that nitrogen may be optionally substituted by a group selected from $R^6$;

$R^3$ is hydrogen;

m is 0;

$R^4$ is selected from halo or methyl;

n is 2; wherein the values of $R^4$ are the same or different;

$R^5$ is $C_{1-6}$alkoxy; and $R^6$ is $C_{1-6}$alkyl;

or a pharmaceutically acceptable salt thereof.

Therefore in a further aspect of the invention there is provided a compound of formula (I) (as depicted above) wherein:

$R^1$ and $R^2$ are independently selected from $C_{1-6}$alkoxy or heterocyclyl; wherein if said heterocyclyl contains an —NH— moiety that nitrogen may be optionally substituted by a group selected from $R^6$; wherein $R^6$ is selected from $C_{1-6}$alkyl;

$R^3$ is hydrogen;

m is 0;

$R^4$ is selected from halo or methyl; and n is 2; wherein the values of $R^4$ are the same or different;

or a pharmaceutically acceptable salt thereof.

Therefore in a further aspect of the invention there is provided a compound of formula (I) (as depicted above) wherein:

$R^1$ and $R^2$ are independently selected from 2-methoxyethoxy, ethoxy, methoxy, 4-ethylpiperazin-1-yl, 4-isopropylpiperazin-1-yl, 4-methylpiperazin-1-yl or 4-tert-butylpiperazin-1-yl;

$R^3$ is hydrogen;

m is 0;

$R^4$ is selected from fluoro, chloro or methyl; and n is 2; wherein the values of $R^4$ are the same or different; or a pharmaceutically acceptable salt thereof.

Therefore in a further aspect of the invention there is provided a compound of formula (I) (as depicted above) wherein:

$R^1$ and $R^2$ are independently selected from methoxy, ethoxy, 1-methylpiperazin-4-yl, 1-ethylpiperazin-4-yl or 1-isopropylpiperazin-4-yl;

$R^3$ is hydrogen;

m is 0;

$R^4$ is selected from fluoro, chloro or methyl; and n is 2; wherein the values of $R^4$ are the same or different;

or a pharmaceutically acceptable salt thereof.

In another aspect of the invention, preferred compounds of the invention are any one of the Examples or a pharmaceutically acceptable salt thereof.

Another aspect of the present invention provides a process for preparing a compound of formula (I) or a pharmaceutically acceptable salt thereof which process (wherein variable groups are, unless otherwise specified, as defined in formula (I)) comprises of:

Process a) reacting a compound of formula (II):

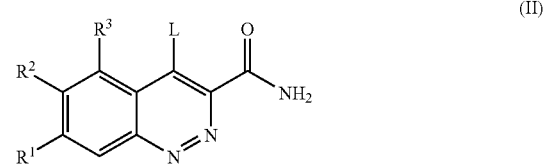

wherein L is a displaceable atom or group; with a compound of formula (III):

or

Process b) reacting a compound of formula (IV):

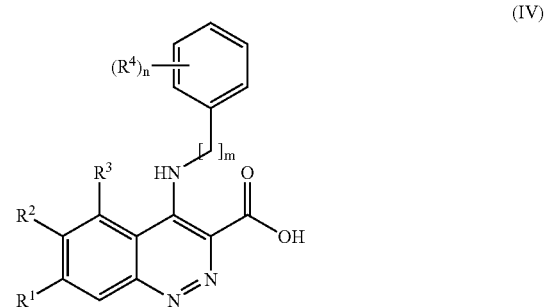

or an activated derivative thereof; with ammonia;

Process c) reacting a compound of formula (V):

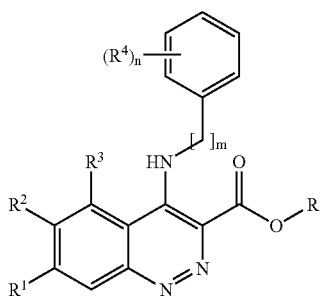
(V)

wherein R is $C_{1-6}$alkyl, in particular methyl and ethyl; with formamide and a base; or Process d) hydrolysis of a compound of formula (VI):

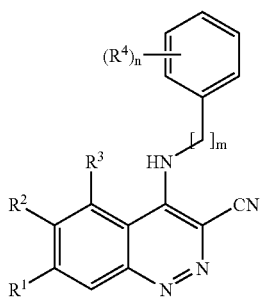
(VI)

or

Process e) for compounds of formula (I) when one of $R^1$ and $R^2$ is a carbon linked group; by reaction of a compound of formula (VIIa) or (VIIb):

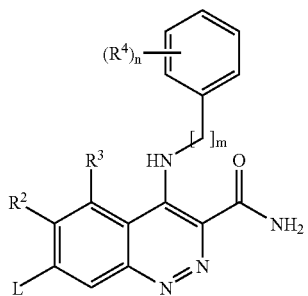
(VIIa)

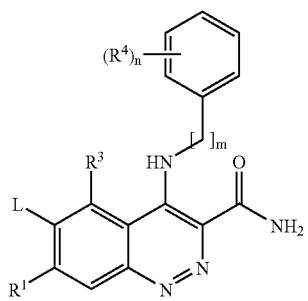
(VIIb)

wherein L is a displaceable group; with a compound of formula (VIIIa) or (VIIIb):

$R^1$—B($R^a$)$_2$  (VIIIa)

$R^2$—B($R^a$)$_2$  (VIIIb)

wherein —B($R^a$)$_2$ is a boronic acid derivative or trialkylborane; or

Process f) for compounds of formula (I) when one of $R^1$ and $R^2$ is a nitrogen linked group; by reaction of a compound of formula (IXa) or (IXb):

(IXa)

(IXb)

wherein L is a displaceable group; with a compound of formula (Xa) or (Xb):

$R^1$—H  (Xa)

$R^2$—H  (Xb)

and thereafter if necessary:

i) converting a compound of the formula (I) into another compound of the formula (I);

ii) removing any protecting groups;

iii) forming a pharmaceutically acceptable salt.

L is a displaceable group, suitable values for L include chloro, bromo, tosyl and trifluoromethylsulphonyloxy.

—B($R^a$)$_2$ is a boronic acid derivative, suitable examples of boronic acid derivatives include dihydroxyboryl, 4,4,5,5-tetramethyl-1,3,2-dioxaborolanyl; a suitable example of a triakylborane is 9-borabicyclo[3.3.1]nonyl.

Specific reaction conditions for the above reactions are as follows.

Process a) Compounds of formula (II) can be reacted with compounds of formula (III) in a solvent such as ethanol or dimethylformamide, usually under thermal conditions often in the range of 70° C. to 100° C., and in some cases catalysed by the addition of acetic acid.

Alternatively, compounds of formula (II) can be reacted with compounds of formula (III) using coupling chemistry utilizing an appropriate catalyst and ligand such as $Pd_2(dba)_3$ and BINAP respectively and a suitable base such as sodium tert-butoxide or cesium carbonate. The reaction usually requires thermal conditions often in the range of 80° C. to 100° C.

Compounds of formula (II) may be prepared by a modification of Scheme 1 or Scheme 2 (see below).

Compounds of formula (III) are commercially available compounds or they are literature compounds or they are readily prepared by processes known to the person skilled in the art.

Process b) Acids of formula (IV) and ammonia may be coupled together in the presence of a suitable coupling reagent. Standard peptide coupling reagents known in the art can be employed as suitable coupling reagents, for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (IV) may be prepared by a modification of Scheme 1 or Scheme 2 (see below).

Process c) Esters of formula (V) may be reacted together with formamide and a base. Preferably this reaction occurs sequentially, addition of the formamide first, followed by the base. Suitable bases are alkoxide bases, for example methoxide and ethoxide bases, eg sodium methoxide. The reaction is typically performed at a temperature of 100° C. in a suitable solvent such as DMF.

Compounds of formula (V) may be prepared according to Scheme 1.

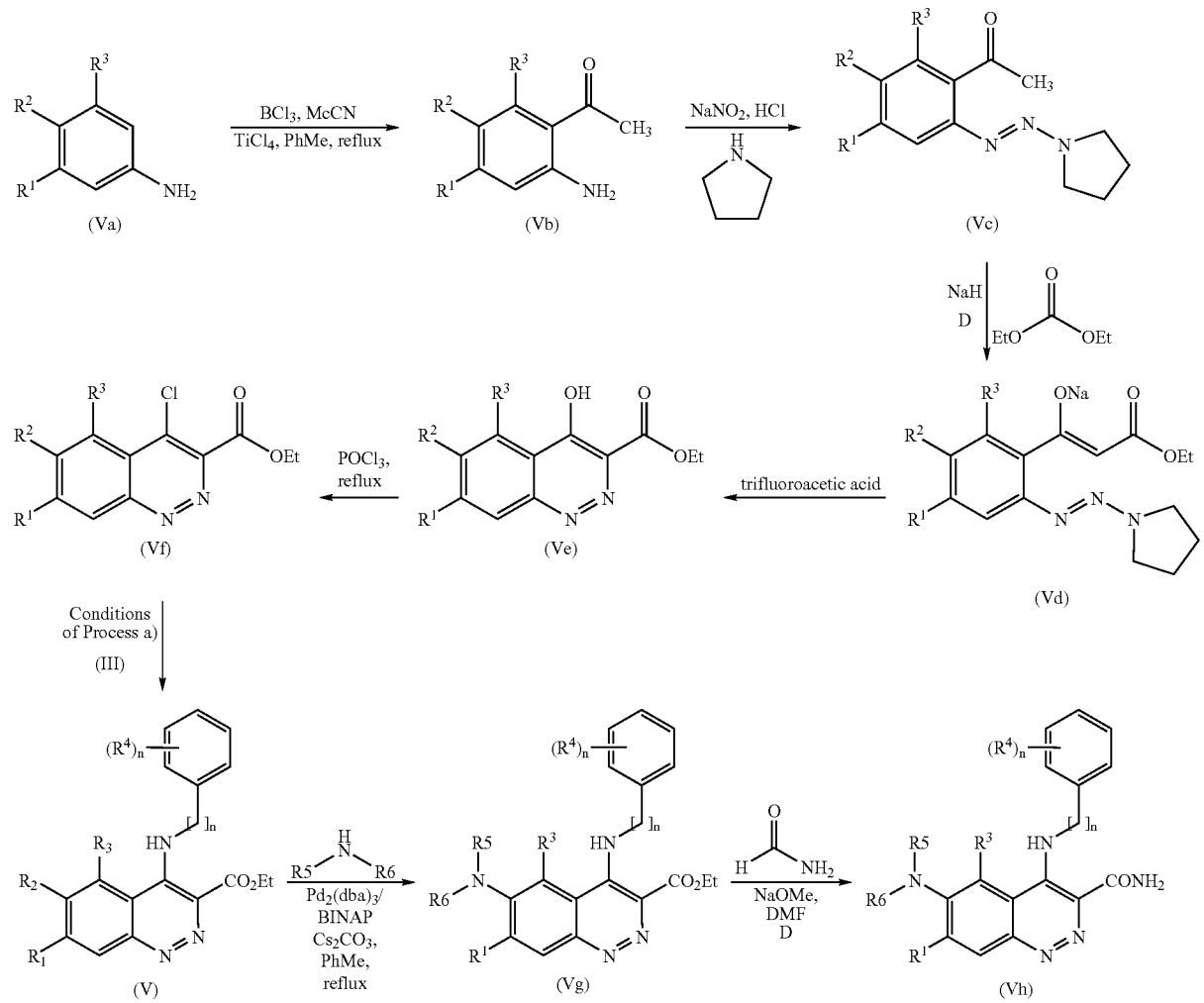

Scheme 1

Compounds of formula (Va) and (Vb) are commercially available compounds or they are literature compounds or they are readily prepared by processes known to the person skilled in the art.

Process d) Compounds of formula (VI) can be hydrolysed under standard acidic or basic conditions.

Compounds of formula (VI) may be prepared by a modification of Scheme 1 or Scheme 2.

Process e) Compounds of formula (VIIa) and (VIIb) can be reacted with boronic acid derivatives of formula (VIIIa) and (VIIIb) using a palladium catalyst and a base. A suitable catalyst is $Pd(PPh_3)_4$ and a suitable base is potassium carbonate. The reaction is typically performed at a temperature of 100° C., or under microwave conditions, in a suitable solvent system such as dioxane/water.

Compounds of formula (VIIa) and (VIIb) can be reacted with trialkylboranes of formula (VIIIa) and (VIIIb) under standard Suzuki conditions, for example using a Pd catalyst in the presence of a base in a suitable solvent, for example, DMF typically at 50° C.

Compounds of formula (VIIa) and (VIIb) may be prepared by a modification of Scheme 1 or Scheme 2.

Compounds of formula (VIIIa) and (VIIIb) are commercially available compounds or they are literature compounds or they are readily prepared by processes known to the person skilled in the art.

Process f) Compounds of formula (IXa) and (IXb) can be reacted with amines of formula (Xa) and (Xb) using a palladium catalyst a ligand and a base. A suitable catalyst is $Pd_2(dba)_3$, a suitable ligand is BINAP and a suitable base is caesium carbonate. The reaction is typically performed at a temperature of 100° C., or under microwave conditions, in a suitable solvent system such as toluene or dimethylacetamide.

Compounds of formula (IXa) and (IXb) may be prepared by a modification of Scheme 1 or Scheme 2.

Compounds of formula (Xa) and (Xb) are commercially available compounds or they are literature compounds or they are readily prepared by processes known to the person skilled in the art.

An alternative scheme for preparing certain compounds of formula (I) which can be modified to prepare certain intermediates described herein above is shown in Scheme 2:

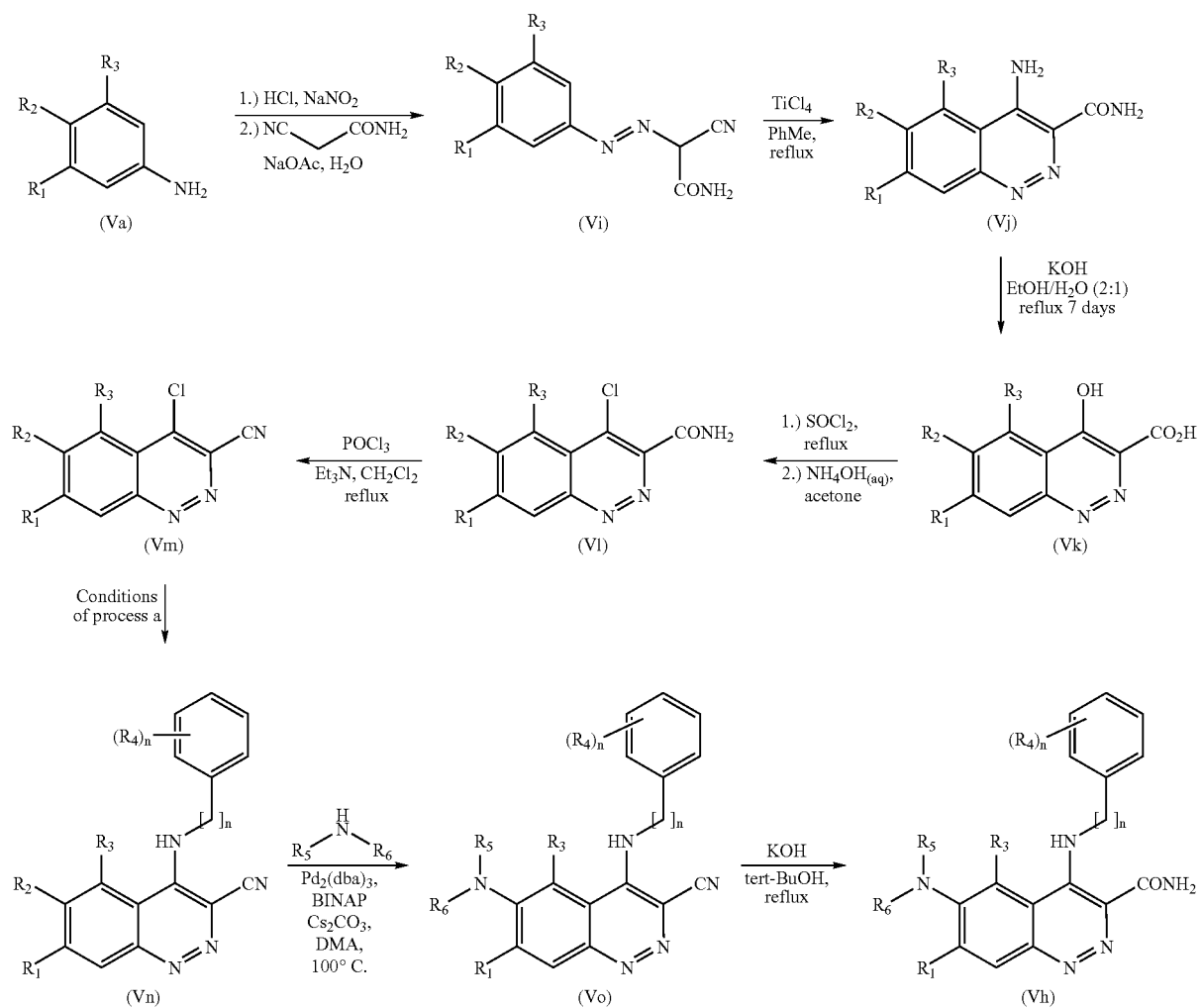

Scheme 2

In some embodiments, the invention relates to a process of producing a compound of formula (I) as disclosed herein comprising reacting a compound of formula (V):

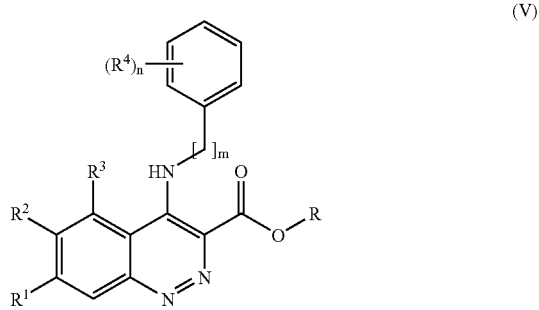

wherein R is $C_{1-6}$alkyl with formamide and a base, such that a compound of formula (I) is formed; and optionally thereafter:

i) converting a compound of the formula (I) into another compound of the formula (I);

ii) removing any protecting groups; or iii) forming a pharmaceutically acceptable salt.

In further embodiments, R is selected from methyl and ethyl.

In some embodiments, the invention relates to a process of producing a compound of formula (I) as disclosed herein comprising hydrolyzing a compound of formula (VI):

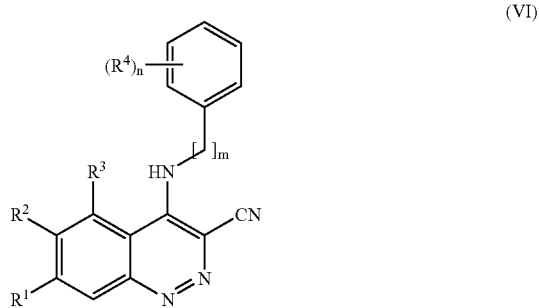

such that a compound of formula (I) is formed; and optionally thereafter:

i) converting a compound of the formula (I) into another compound of the formula (I);

ii) removing any protecting groups; or iii) forming a pharmaceutically acceptable salt.

In further embodiments, hydrolyzing is performed by mixing a compound of formula (VI) with a metal hydroxide and a branched alkyl alcohol.

In further embodiments, said metal hydroxide is potassium hydroxide.

In further embodiments, said branched alkyl alcohol is a tertiary alcohol such as tert-butyl alcohol.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain intermediates described herein are novel and these are provided as a further feature of the invention.

As stated hereinbefore the compounds defined in the present invention possess anti-cancer activity which is believed to arise from the CSF-1R kinase inhibitory activity of the compounds. These properties may be assessed, for example, using the procedure set out below.

In some embodiments, the invention relates to a method of treating cancer comprising providing a subject at risk for, diagnosed with, or exhibiting symptoms of cancer and administering a pharmaceutical composition comprising a compound of formula (I) as disclosed herein to said subject.

In some embodiments, the invention relates to a method of inhibiting CSF-1R kinase comprising providing a CSF-1R kinase and a compound of formula (I) as disclosed herein, and mixing under conditions such that CSF-1R kinase is inhibited.

Biological Activity

Assay 1: CSF-1R In Vitro AlphaScreen Assay

Activity of purified CSF-1R was determined in vitro using an Amplified Luminescent Proximity Homogeneous Assay (ALPHA)(Perkin Elmer), which measures phosphorylation of the CSF-1R substrate, biotinylated poly-glutamine-tyrosine peptide (pEY-HTRF CisBio 61GT0BLD), as described below. The His-tagged kinase domain of CSF-1R (i.e., amino acids 568-912, GeneBank ID NM_005211; (see page 25 lines 13-19 of WO 2006/067445 for the sequence listing)) was purified from baculovirus infected SF+Express insect cells (1.4×106 cells/ml), French pressed and chromatographed through subsequent Qiagen Ni-NTA, Superflow Mono Q HR 10/10, and Superdex 200 SEC columns. Typical yield was 245 μg/l of cell pellet at >95% purity.

The phosphorylation of the CSF-1R substrate in the presence and absence of the compound of interest was determined. Briefly, 0.57 nM of purified CSF-1R, 5 nM pEY substrate, and compound were preincubated in 1× buffer for 30 minutes at 25° C. Reactions were initiated with addition of 90 μM adenosine triphosphate (ATP) in 1× buffer and incubated at 25° C. for 60 minutes and reactions stopped by addition of 5 μl of detection mix consisting of 136 mM NaCl, 102 mM ethylenediamine tetraacetic acid, 1.65 mg/ml BSA, 40 ug/ml Streptavidin donor beads (Perkin Elmer 6760002), 40 ug/ml pTyr100 acceptor beads (Perkin Elmer 6760620). Plates were incubated at 25° C. for 18 hours in the dark. Phosphorylated substrate was detected by an EnVision plate reader (Perkin Elmer) 680 nm excitation, 520-620 nm emission. Data was graphed and $IC_{50}$s calculated using Excel Fit (Microsoft).

Assay 2: CSF1R In-Vitro AlphaScreen Assay

Activity of purified CSF-1R was determined in-vitro using an Amplified Luminescent Proximity Homogeneous Assay (ALPHA) (Perkin Elmer, Mass.), which measures phosphorylation of CSF-1R substrate, biotinylated poly-glutamine-tyrosine peptide (pEY-HTRF CisBio 61GT0BLD), as described below. The His-tagged kinase domain of CSF-1R (i.e., amino acids 568-912, GeneBank ID NM_005211) was purified from baculovirus infected SF+Express insect cells (1.4×106 cells/ml), French pressed and chromatographed through subsequent QIAgen Ni-NTA, Superflow Mono Q HR 10/10, and Superdex 200 SEC columns. Typical yield was 322 ug/l of cell pellet at >95% purity.

The phosphorylation of the CSF-1R substrate in the presence and absence of the compound of interest was determined. Briefly, 5 ul of Enzyme/Substrate/adenosine triphosphate (ATP) mix consisting of 0.46 nM of purified CSF-1R, 12 nM pEY substrate, and 12 mM ATP in 1.2× buffer was preincubated with 2 ul of compound for 20 minutes at 25° C. Reactions were initiated with 5 ul of Metal mix consisting of 24 mM $MgCl_2$ in 1.2× buffer and incubated at 25° C. for 90 minutes and reactions were stopped by addition of 5 ul of Detection mix consisting of 20 mM HEPES, 102 mM ethylenediamine tetraacetic acid, 1.65 mg/ml BSA, 136 mM NaCl, 40 ug/ml Streptavidin donor beads (Perkin Elmer, Mass., Catalog #6760002), and 40 ug/ml phosphotyrosine-specific antibody coated acceptor beads (Perkin Elmer, Mass., Catalog #6760620). Plates were incubated at 25° C. for 18 hours in the dark. Phosphorylated substrate was detected by an EnVision plate reader (Perkin Elmer) 680 nm excitation, 520-620 nm emission. Data was graphed and $IC_{50}$s calculated using Excel Fit (Microsoft).

When tested in one or other of the above in vitro assays, the compounds of the present invention generally exhibited activity less than 30 μM. For example the following results were obtained in an assay substantially similar to one or other of the assays described hereinabove:

| Example No | Assay 1 $IC_{50}$ | Assay 2 $IC_{50}$ |
| --- | --- | --- |
| 1 | <3 nM | |
| 2 | 8 nM | |
| 3 | <3 nM | |
| 4 | 5 nM | |
| 5 | <3 nM | |
| 6 | <3 nM | |
| 7 | <4 nM | |
| 8 | 3 nM | |
| 9 | <15 nM | |
| 10 | <3 nM | |
| 11 | 8 nM | |
| 12 | 5 nM | |
| 13 | <3 nM | |
| 14 | <3 nM | |
| 15 | <4 nM | |
| 16 | 9 nM | |
| 17 | <3 nM | |
| 18 | <3 nM | |
| 19 | <3 nM | |
| 20 | <3 nM | |
| 21 | <3 nM | |
| 22 | <3 nM | |
| 23 | <5 nM | |
| 24 | <3 nM | |
| 25 | <3 nM | |
| 26 | 51 nM | |
| 27 | <3 nM | |
| 28 | <3 nM | |
| 29 | | 7 nM |
| 30 | | 10 nM |
| 31 | | 13 nM |
| 32 | | 8 nM |
| 33 | | 12 nM |
| 34 | | 5 nM |
| 35 | | <9 nM |
| 36 | | <3 nM |
| 37 | | 71 nM |

-continued

| Example No | Assay 1 IC$_{50}$ | Assay 2 IC$_{50}$ |
|---|---|---|
| 38 | | <3 nM |
| 39 | | <3 nM |
| 40 | | <3 nM |
| 41 | | <3 nM |
| 42 | | 7 nM |
| 43 | | 3 nM |
| 44 | | 16 nM |
| 45 | | 6 nM |
| 46 | | |
| 47 | | 6 nM |
| 48 | | <3 nM |
| 49 | | 20 nM |
| 50 | | 33 nM |
| 51 | | |
| 52 | | |
| 53 | | |
| 54 | | |

According to a further aspect of the invention there is provided a pharmaceutical composition which comprises a compound of the formula (I), or a pharmaceutically acceptable salt thereof, as defined hereinbefore, in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 1-1000 mg/kg, and this normally provides a therapeutically-effective dose. Preferably a daily dose in the range of 10-100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt thereof, as defined hereinbefore for use in a method of treatment of the human or animal body by therapy.

We have found that the compounds defined in the present invention, or a pharmaceutically acceptable salt thereof, are effective anti-cancer agents which property is believed to arise from their CSF-1R kinase inhibitory properties. Accordingly the compounds of the present invention are expected to be useful in the treatment of diseases or medical conditions mediated alone or in part by CSF-1R kinase, i.e. the compounds may be used to produce a CSF-1R kinase inhibitory effect in a warm-blooded animal in need of such treatment.

Thus the compounds of the present invention provide a method for treating cancer characterised by inhibition of CSF-1R kinase, i.e. the compounds may be used to produce an anti-cancer effect mediated alone or in part by the inhibition of CSF-1R kinase.

Such a compound of the invention is expected to possess a wide range of anti-cancer properties as aberrant expression of CSF 1R and/or CSF 1 has been observed in multiple human cancers and derived cell lines, including but not limited to, breast, ovarian, endometrial, prostate, lung, kidney and pancreatic tumors as well as haematological malignancies including, but not limited to, myelodysplastic syndrome, acute myelogenous leukemia, chronic myelogenous leukemia, non Hodgkin's lymphoma, Hodgkin's disease, multiple myeloma and chronic lymphocytic leukemia. Activating mutations have also been reported in haematopoietic and lymphoid tissue and lung cancer. Further, tumor associated macrophages have been associated with poor prognosis in multiple tumor types including, but not limited to, breast, endometrial, kidney, lung, bladder and cervical cancers, glioma, squamous cell carcinoma of the esophagus, malignant uveal melanoma and follicular lymphoma. It is expected that a compound of the invention will possess anticancer activity against these cancers through direct effect on the tumor and/or indirectly through effect on tumor associated macrophages.

In a further aspect of the invention, compounds of formula (I) may be also be of value in the treatment of certain additional indications. These indications include, but are not limited to tumor-associated osteolysis, osteoporosis including ovariectomy-induced bone loss, orthopedic implant failure, autoimmune disorders including systemic lupus erythematosus, arthritis including rheumatoid arthritis, osteoarthritis, renal inflammation and glomerulonephritis; inflammatory bowel disease; transplant rejection including renal and bone marrow allografts and skin xenograft, atherosclerosis, obesity, Alzheimer's Disease and Langerhans cell histiocytosis. A further aspect of the present invention therefore includes the treatment of one of more of these diseases, particularly arthritis including rheumatoid arthritis and osteoarthritis. These indications also include, but are not limited to chronic obstructive pulmonary disease, diabetes and chronic skin disorders including psoriasis.

Thus according to this aspect of the invention there is provided a compound of the formula (I), or a pharmaceutically acceptable salt thereof, as defined hereinbefore for use as a medicament.

According to a further aspect of the invention there is provided the use of a compound of the formula (I), or a pharmaceutically acceptable salt thereof, as defined hereinbefore in the manufacture of a medicament for use in the production of a CSF-1R kinase inhibitory effect in a warm-blooded animal such as man.

According to this aspect of the invention there is provided the use of a compound of the formula (I), or a pharmaceutically acceptable salt thereof, as defined hereinbefore in the manufacture of a medicament for use in the production of an anti-cancer effect in a warm-blooded animal such as man.

According to a further feature of the invention, there is provided the use of a compound of the formula (I), or a pharmaceutically acceptable salt thereof, as defined herein before in the manufacture of a medicament for use in the treatment of breast, ovarian, bladder, cervical, endometrial, prostate, lung, kidney and pancreatic tumors; haematological malignancies including myelodysplastic syndrome, acute myelogenous leukemia, chronic myelogenous leukemia, non Hodgkin's lymphoma, Hodgkin's disease, multiple myeloma and chronic lymphocytic leukemia; and glioma, squamous cell carcinoma of the esophagus, malignant uveal melanoma and follicular lymphoma.

According to a further feature of the invention, there is provided the use of a compound of the formula (I), or a pharmaceutically acceptable salt thereof, as defined herein before in the manufacture of a medicament for use in the treatment of tumor-associated osteolysis, osteoporosis including ovariectomy-induced bone loss, orthopedic implant failure, autoimmune disorders including systemic lupus erythematosus, arthritis including rheumatoid arthritis, osteoarthritis, renal inflammation and glomerulonephritis; inflammatory bowel disease; transplant rejection including renal and bone marrow allografts and skin xenograft, atherosclerosis, obesity, Alzheimer's Disease, chronic obstructive pulmonary disease, diabetes and chronic skin disorders including psoriasis and Langerhans cell histiocytosis According to a further feature of this aspect of the invention there is provided a method for producing a CSF-1R kinase inhibitory effect in a warm-blooded animal, such as man, in need of such treatment which comprises administering to said animal an effective amount of a compound of formula (I), or a pharmaceutically acceptable salt thereof, as defined above.

According to a further feature of this aspect of the invention there is provided a method for producing an anti-cancer effect in a warm-blooded animal, such as man, in need of such treatment which comprises administering to said animal an effective amount of a compound of formula (I), or a pharmaceutically acceptable salt thereof, as defined above.

According to an additional feature of this aspect of the invention there is provided a method of treating breast, ovarian, bladder, cervical, endometrial, prostate, lung, kidney and pancreatic tumors; haematological malignancies including myelodysplastic syndrome, acute myelogenous leukemia, chronic myelogenous leukemia, non Hodgkin's lymphoma, Hodgkin's disease, multiple myeloma and chronic lymphocytic leukemia; and glioma, squamous cell carcinoma of the esophagus, malignant uveal melanoma and follicular lymphoma in a warm-blooded animal, such as man, in need of such treatment which comprises administering to said animal an effective amount of a compound of formula (I) or a pharmaceutically acceptable salt thereof as defined herein before.

According to an additional feature of this aspect of the invention there is provided a method of treating tumor-associated osteolysis, osteoporosis including ovariectomy-induced bone loss, orthopedic implant failure, autoimmune disorders including systemic lupus erythematosus, arthritis including rheumatoid arthritis, osteoarthritis, renal inflammation and glomerulonephritis; inflammatory bowel disease; transplant rejection including renal and bone marrow allografts and skin xenograft, atherosclerosis, obesity, Alzheimer's Disease, chronic obstructive pulmonary disease, diabetes and chronic skin disorders including psoriasis and Langerhans cell histiocytosis in a warm-blooded animal, such as man, in need of such treatment which comprises administering to said animal an effective amount of a compound of formula (I) or a pharmaceutically acceptable salt thereof as defined herein before.

In a further aspect of the invention there is provided a pharmaceutical composition which comprises a compound of the formula (I), or a pharmaceutically acceptable salt thereof, as defined herein before in association with a pharmaceutically-acceptable diluent or carrier for use in the production of a CSF-1R kinase inhibitory effect in a warm-blooded animal such as man.

In a further aspect of the invention there is provided a pharmaceutical composition which comprises a compound of the formula (I), or a pharmaceutically acceptable salt thereof, as defined herein before in association with a pharmaceutically-acceptable diluent or carrier for use in the production of an anti-cancer effect in a warm-blooded animal such as man.

In a further aspect of the invention there is provided a pharmaceutical composition which comprises a compound of the formula (I), or a pharmaceutically acceptable salt thereof, as defined herein before in association with a pharmaceutically-acceptable diluent or carrier for use in the treatment of breast, ovarian, bladder, cervical, endometrial, prostate, lung, kidney and pancreatic tumors; haematological malignancies including myelodysplastic syndrome, acute myelogenous leukemia, chronic myelogenous leukemia, non Hodgkin's lymphoma, Hodgkin's disease, multiple myeloma and chronic lymphocytic leukemia; and glioma, squamous cell carcinoma of the esophagus, malignant uveal melanoma and follicular lymphoma in a warm-blooded animal such as man.

In a further aspect of the invention there is provided a pharmaceutical composition which comprises a compound of the formula (I), or a pharmaceutically acceptable salt thereof, as defined herein before in association with a pharmaceutically-acceptable diluent or carrier for use in the treatment of tumor-associated osteolysis, osteoporosis including ovariectomy-induced bone loss, orthopedic implant failure, autoimmune disorders including systemic lupus erythematosus, arthritis including rheumatoid arthritis, osteoarthritis, renal inflammation and glomerulonephritis; inflammatory bowel disease; transplant rejection including renal and bone marrow allografts and skin xenograft, atherosclerosis, obesity, Alzheimer's Disease, chronic obstructive pulmonary disease, diabetes and chronic skin disorders including psoriasis and Langerhans cell histiocytosis in a warm-blooded animal such as man.

According to a further aspect of the invention there is provided the use of a compound of the formula (I), or a pharmaceutically acceptable salt thereof, as defined hereinbefore in the production of a CSF-1R kinase inhibitory effect in a warm-blooded animal such as man.

According to this aspect of the invention there is provided the use of a compound of the formula (I), or a pharmaceutically acceptable salt thereof, as defined hereinbefore in the production of an anti-cancer effect in a warm-blooded animal such as man.

According to a further feature of the invention, there is provided the use of a compound of the formula (I), or a pharmaceutically acceptable salt thereof, as defined herein before in the treatment of breast, ovarian, bladder, cervical, endometrial, prostate, lung, kidney and pancreatic tumors; haematological malignancies including myelodysplastic syndrome, acute myelogenous leukemia, chronic myelogenous leukemia, non Hodgkin's lymphoma, Hodgkin's disease, multiple myeloma and chronic lymphocytic leukemia; and glioma, squamous cell carcinoma of the esophagus, malignant uveal melanoma and follicular lymphoma.

According to a further feature of the invention, there is provided the use of a compound of the formula (I), or a pharmaceutically acceptable salt thereof, as defined herein before in the treatment of tumor-associated osteolysis, osteoporosis including ovariectomy-induced bone loss, orthopedic implant failure, autoimmune disorders including systemic lupus erythematosus, arthritis including rheumatoid arthritis, osteoarthritis, renal inflammation and glomerulonephritis; inflammatory bowel disease; transplant rejection including renal and bone marrow allografts and skin xenograft, atherosclerosis, obesity, Alzheimer's Disease, chronic obstructive pulmonary disease, diabetes and chronic skin disorders including psoriasis and Langerhans cell histiocytosis.

The CSF-1R kinase inhibitory treatment defined hereinbefore may be applied as a sole therapy or may involve, in addition to the compound of the invention, conventional surgery or radiotherapy or chemotherapy. Such chemotherapy may include one or more of the following categories of antitumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy) quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies;

(x) Cell cycle inhibitors including for example CDK inhibitors (eg flavopiridol) and other inhibitors of cell cycle checkpoints (eg checkpoint kinase); inhibitors of aurora kinase and other kinases involved in mitosis and cytokinesis regulation (eg mitotic kinesins); and histone deacetylase inhibitors; and (xi) endothelin antagonists, including endothelin A antagonists, endothelin B antagonists and endothelin A and B antagonists; for example ZD4054 and ZD1611 (WO 96 40681), atrasentan and YM598.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of CSF-1R kinase in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non-limiting examples in which, unless stated otherwise:

(i) temperatures are given in degrees Celsius (° C.); operations were carried out at room or ambient temperature unless otherwise stated, that is, at a temperature in the range of 18-25° C.;

(ii) organic solutions were dried over anhydrous sodium sulphate or magnesium sulphate; evaporation of solvent was carried out using a rotary evaporator under reduced pressure (600-4000 Pascals; 4.5-30 mmHg) with a bath temperature of up to 60° C.;

(iii) in general, the course of reactions was followed by TLC and reaction times are given for illustration only;

(iv) final products had satisfactory proton nuclear magnetic resonance (NMR) spectra and/or mass spectral data;

(v) yields are given for illustration only and are not necessarily those which can be obtained by diligent process development; preparations were repeated if more material was required;

(vii) when given, NMR data is in the form of delta values for major diagnostic protons, given in parts per million (ppm)

relative to tetramethylsilane (TMS) as an internal standard, determined at 400 MHz using perdeuterio dimethyl sulphoxide (DMSO-$d_6$) as solvent unless otherwise indicated;

(vii) chemical symbols have their usual meanings; SI units and symbols are used;

(viii) solvent ratios are given in volume:volume (v/v) terms; and (ix) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(MH)^+$;

(x) where a synthesis is described as being analogous to that described in a previous example the amounts used are the millimolar ratio equivalents to those used in the previous example;

(xi) "H-Cube" refers to the H-Cube continuous hydrogenation equipment manufactured by Thales Nanotechnology and (xii) the following abbreviations have been used:

| | |
|---|---|
| DMA | N,N-dimethylacetamide |
| DMF | N,N-dimethylformamide; |
| EtOAc | ethyl acetate; |
| MeOH | methanol; |
| THF | tetrahydrofuran; |
| TFA | trifluoroacetic acid; |
| DMSO | dimethylsulphoxide; and |
| DCM | dichloromethane. |

Example 1

4-[(2,4-Difluorophenyl)amino]-6,7-dimethoxycinnoline-3-carboxamide

To a 25 mL round bottom flask charged with a magnetic stir bar was added ethyl 4-[(2,4-difluorophenyl)amino]-6,7-dimethoxycinnoline-3-carboxylate (0.195 g, 0.50 mmol) (Method 27), anhydrous DMF (3 mL), formamide (0.135 g, 3 mmol), and 3 mL of a 0.5 M solution of sodium methoxide in MeOH. The reaction was warmed to 100° C. for 2 h before being allowed to cool to rt. The reaction was poured over water (~50 mL) and the crude product precipitated from solution. The solid was collected via vacuum filtration using a Buchner funnel and was purified on 40 g silica using EtOAc/MeOH (4:1) as eluent providing 0.174 g (96%) of the title compound as a white solid. $^1$H NMR: 11.35 (s, 1H), 8.86 (s, 1H), 8.05 (s, 1H), 7.71 (s, 1H), 7.48 (m, 1H), 7.38 (m, 1H), 7.18 (m, 1H), 6.69 (s, 1H), 4.06 (s, 3H), 3.50 (s, 3H); m/z 361.

Examples 2-12

The following examples were prepared according to the procedure in Example 1 using the appropriate starting material, and were purified either by silica gel chromatography or semi-preparative reverse phase HPLC.

| Ex. | Compound | $^1$H NMR (300 MHz) | m/z | Starting Material |
|---|---|---|---|---|
| 2 | 4-[(2-Fluoro-4-methylphenyl)amino]-6,7-dimethoxycinnoline-3-carboxamide | 11.26 (s, 1H), 8.80 (s, 1H), 7.95 (s, 1H), 7.65 (s, 1H), 7.15 (m, 2H), 7.05 (d, 1H), 6.62 (s, 1H), 4.00 (s, 3H), 3.37 (s, 3H), 2.30 (s, 3H) | 357 | ethyl 4-[(2-fluoro-4-methylphenyl)amino]-6,7-dimethoxycinnoline-3-carboxylate (Method 29) |
| 3 | 4-[(3-Chloro-2-fluorophenyl)amino]-6,7-dimethoxycinnoline-3-carboxamide | 11.35 (s, 1H), 8.85 (s, 1H), 8.05 (s, 1H), 7.70 (s, 1H), 7.35 (t, 1H), 7.17 (t, 1H), 7.05 (t, 1H), 6.70 (s, 1H), 4.05 (s, 3H), 3.48 (s, 3H) | 378 | ethyl 4-[(3-chloro-2-fluorophenyl)amino]-6,7-dimethoxycinnoline-3-carboxylate (Method 30) |
| 4 | 4-[(2-Fluoro-5-methylphenyl)amino]-6,7-dimethoxycinnoline-3-carboxamide | 11.30 (s, 1H), 8.80 (s, 1H), 7.98 (s, 1H), 7.65 (s, 1H), 7.20 (m, 1H), 7.03 9m, 2H), 6.65 (s, 1H), 4.00 (s, 3H), 3.40 (s, 3H), 2.22 (s, 3H) | 357 | ethyl 4-[(2-fluoro-5-methylphenyl)amino]-6,7-dimethoxycinnoline-3-carboxylate (Method 31) |
| 5 | 4-[(2,3-Dichlorophenyl)amino]-6,7-dimethoxycinnoline-3-carboxamide | 11.50 (s, 1H), 8.89 (s, 1H), 8.05 (s, 1H), 7.71 (s, 1H), 7.40 (d, 1H), 7.25 (t, 1H), 6.90 (d, 1H), 6.55 (s, 1H), 4.00 (s, 3H), 3.50 (s, 3H) | 394 | ethyl 4-[(2,3-dichlorophenyl)amino]-6,7-dimethoxycinnoline-3-carboxylate (Method 32) |
| 6 | 7-Ethoxy-4-[(2-fluoro-5-methylphenyl)amino]-6-(4-methylpiperazin-1-yl)cinnoline-3-carboxamide | 8.78 (s, 1H), 7.85 (s, 1H), 7.56 (s, 1H), 7.31-7.15 (m, 2H), 7.03 (d, 2H), 6.64 (s, 1H), 4.26 (q, 2H), 2.76 (s, 4H), 2.33 (s, 4H), 2.27 (s, 3H), 2.12 (s, 3H), 1.42 (t, 3H) | 440 | ethyl 7-ethoxy-4-[(2-fluoro-5-methylphenyl)amino]-6-(4-methylpiperazin-1-yl)cinnoline-3-carboxylate (Method 47) |

-continued

| Ex. | Compound | ¹H NMR (300 MHz) | m/z | Starting Material |
|---|---|---|---|---|
| 7 | 4-[(2,4-Difluorophenyl)amino]-7-ethoxy-6-(4-methylpiperazin-1-yl)cinnoline-3-carboxamide | 11.90 (s, br, 1H), 8.62 (s, 1H), 8.07 (s, 1H), 7.60 (s, 1H), 7.50 (m, 2H), 7.20 (m, 1H), 7.00 (s, br, 1H), 4.30 (q, 2H), 3.50 (m, 4H), 3.13 (m, 2H), 2.90 (m, 2H), 3.80 (d, 3H), 1.50 (t, 3H) | 443 | ethyl 4-[(2,4-difluorophenyl)amino]-7-ethoxy-6-(4-methylpiperazin-1-yl)cinnoline-3-carboxylate (Method 48) |
| 8 | 4-[(2,3-Dichlorophenyl)amino]-7-ethoxy-6-(4-methylpiperazin-1-yl)cinnoline-3-carboxamide | 11.48 (s, 1H), 8.84 (s, 1H), 8.01 (s, 1H), 7.61 (s, 1H), 7.41 (s, 1H), 7.26 (t, 1H), 6.94 (s, 1H), 6.45 (s, 1H), 4.28 (d, 2H), 2.81 (s, 4H), 2.33 (s, 4H), 2.15 (s, 3H), 1.42 (t, 3H) | 476 | ethyl 4-[(2,3-dichlorophenyl)amino]-7-ethoxy-6-(4-methylpiperazin-1-yl)cinnoline-3-carboxylate (Method 49) |
| 9 | 4-[(3-Chloro-2-fluoro-phenyl)amino]-7-ethoxy-6-(4-methylpiperazin-1-yl)cinnoline-3-carboxamide | 11.36 (s, 1H), 8.83 (s, 1H), 8.00 (s, 1H), 7.60 (s, 1H), 7.38 (t, 1H), 7.17 (d, 2H), 6.58 (s, 1H), 4.28 (q, 2H), 2.80 (s, 4H), 2.32 (s, 4H), 2.15 (s, 3H), 1.42 (t, 3H) | 460 | ethyl 4-[(3-chloro-2-fluoro-phenyl)amino]-7-ethoxy-6-(4-methylpiperazin-1-yl)cinnoline-3-carboxylate (Method 50) |
| 10 | 7-Ethoxy-4-[(2-fluoro-4-methyl-phenyl)amino]-6-(4-methylpiperazin-1-yl)cinnoline-3-carboxamide | 11.27 (s, 1H), 8.75 (s, 1H), 7.91 (s, 1H), 7.53 (s, 1H), 7.18 (d, 2H), 7.05 (s, 1H), 6.59 (s, 1H), 4.25 (d, 2H), 2.74 (s, 4H), 2.32 (s, 7H), 2.17 (s, 3H), 1.41 (t, 3H) | 439 | ethyl 7-ethoxy-4-[(2-fluoro-4-methyl-phenyl)amino]-6-(4-methylpiperazin-1-yl)cinnoline-3-carboxylate (Method 51) |
| 11 | 4-[(2,4-Difluorophenyl)amino]-7-ethoxy-6-(4-propan-2-ylpiperazin-1-yl)cinnoline-3-carboxamide | 11.25 (s, 1H), 8.78 (s, 1H), 7.94 (s, 1H), 7.56 (s, 1H), 7.38-7.50 (m, 1H), 7.24-7.38 (m, 1H), 7.02-7.17 (m, 1H), 6.55 (s, 1H), 4.26 (q, 2H), 2.78 (s, 4H), 2.60-2.64 (m, 1H), 2.47 (s, 4H), 1.42 (t, 3H), 0.96 (d, 6H) | 472 | ethyl 4-[(2,4-difluorophenyl)amino]-7-ethoxy-6-(4-propan-2-ylpiperazin-1-yl)cinnoline-3-carboxylate (Method 52) |
| 12 | 4-[(2,4-Difluorophenyl)amino]-7-ethoxy-6-(4-ethylpiperazin-1-yl)cinnoline-3-carboxamide | 11.20 (s, 1H), 7.90 (s, 1H), 7.50 (s, 1H), 7.39 (t, 1H), 7.25 (t, 1H), 7.06 (t, 1H), 6.51 (s, 1H), 4.25 (q, 2H), 3.30 (q, 2H), 2.70 (s, 4H), 2.30 (s, 4H), 1.37 (t, 3H), 0.90 (t, 3H) | 457 | ethyl 4-[(2,4-difluorophenyl)amino]-7-ethoxy-6-(4-ethylpiperazin-1-yl)cinnoline-3-carboxylate (Method 53) |

Examples 6-12 were in some cases also prepared from the appropriate intermediates according to procedures similar to those described for Example 13 and Methods 47, 27 and 24.

Example 13

4-(2-Fluoro-4-methylphenylamino)-7-methoxy-6-(4-methylpiperazin-1-yl)cinnoline-3-carboxamide A 100 mL round bottom flask was charged with 4-(2-fluoro-4-methylphenylamino)-7-methoxy-6-(4-methylpiperazin-1-yl)cinnoline-3-carbonitrile (Method 60) (360 mg, 0.89 mmol) and potassium hydroxide (4.9 g, 88.6 mmol). Anhydrous tert-butyl alcohol (30 ml) was added and the reaction was heated at vigorous reflux 1 h before being allowed to cool to rt. The reaction mixture was then poured into a separatory funnel containing water (~100 mL) and extracted with EtOAc (2×200 mL). The combined organic layer was washed with sat'd aqueous NaCl (~100 mL), dried with MgSO₄, filtered, and conc. in vacuo to give the crude product which was purified via silica gel chromatography (40 g) using EtOAc/MeOH (1:1) as eluent to give the title compound as a yellow solid. The solid was then recrystallized from 5 mL of MeOH which provided pure title compound (184 mg, 48.9%) as a pale yellow solid. ¹HNMR: 11.60 (s, 1H), 8.55 (s, 1H), 7.85 (s, 1H), 7.16 (s, 1H), 7.37 (m, 2H), 7.10 (m, 1H), 6.21 (s, 1H), 4.05 (s, 3H), 2.46 (s, br, 4H), 2.70-2.60 (m, 7H), 2.35 (s, 3H); m/z 425.

Examples 14-46

The following examples were prepared according to the procedure of Example 13 using the appropriate starting material and purified by silica gel chromatography or semi-preparative reverse phase HPLC. The resulting materials were subsequently recrystallized where necessary.

| Example | Compound | ¹H NMR (300 MHz) | m/z | Starting Material |
|---------|----------|------------------|-----|-------------------|
| 14 | 4-[(3-Chloro-2-fluorophenyl)amino]-7-methoxy-6-(4-methylpiperazin-1-yl)cinnoline-3-carboxamide | 11.38 (s, 1H), 8.84 (s, 1H), 8.00 (s, 1H), 7.64 (s, 1H), 7.39 (s, 1H), 7.09-7.24 (m, 2H), 6.60 (s, 1H), 4.02 (s, 3H), 2.79 (s, 4H), 2.35 (s, 4H), 2.17 (s, 3H) | 446 | 4-[(3-chloro-2-fluorophenyl)amino]-7-methoxy-6-(4-methylpiperazin-1-yl)cinnoline-3-carbonitrile Method 54 |
| 15 | 4-[(2-Fluoro-4-methylphenyl)amino]-6-(4-isopropylpiperazin-1-yl)-7-methoxycinnoline-3-carboxamide | 11.29 (s, 1H), 8.77 (s, 1H), 7.91 (s, 1H), 7.56 (s, 1H), 7.17 (t, 2H), 7.04 (d, 1H), 6.60 (s, 1H), 3.99 (s, 3H), 2.69 (s, 4H), 2.55-2.66 (m, 1H), 2.42 (s, 4H), 2.32 (s, 3H), 0.94 (d, 6H) | 453 | 4-[(2-fluoro-4-methylphenyl)amino]-6-(4-isopropylpiperazin-1-yl)-7-methoxycinnoline-3-carbonitrile Method 55 |
| 16 | 6-(4-tert-Butylpiperazin-1-yl)-4-[(2-fluoro-4-methylphenyl)amino]-7-methoxycinnoline-3-carboxamide | 11.31 (s, 1H), 8.76 (s, 1H), 7.90 (s, 1H), 7.56 (s, 1H), 7.13-7.24 (m, 2H), 7.06 (s, 1H), 6.59 (s, 1H), 3.99 (s, 3H), 2.69 (s, 4H), 2.50 (s, 4H), 2.32 (s, 3H), 0.99 (s, 9H) | 467 | 6-(4-tert-butylpiperazin-1-yl)-4-[(2-fluoro-4-methylphenyl)amino]-7-methoxycinnoline-3-carbonitrile Method 56 |
| 17 | 4-[(2,4-Difluorophenyl)amino]-7-(2-methoxyethoxy)-6-(4-methylpiperazin-1-yl)cinnoline-3-carboxamide | 10.65 (s, br, 1H), 8.60 (s, 1H), 7.95 (s, 1H), 7.68 (s, 1H), 7.39 (m, 2H), 7.10 (t, 1H), 6.82 (s, br, 1H), 4.30 (s, 2H), 3.75 (s, 2H), 3.65 (m, 2H), 3.40 (m, 2H), 3.30 (s, 3H), 3.05 (m, 2H), 2.80 (m, 2H), 2.72 (s, 3H) | 473 | 4-[(2,4-difluorophenyl)amino]-7-(2-methoxyethoxy)-6-(4-methylpiperazin-1-yl)cinnoline-3-carbonitrile Method 61 |
| 18 | 4-[(2-Fluoro-4-methylphenyl)amino]-7-(2-methoxyethoxy)-6-(4-methylpiperazin-1-yl)cinnoline-3-carboxamide | 10.90 (s, br, 1H), 8.64 (s, 1H), 8.03 (s, 1H), 7.58 (s, 1H), 7.28 (m, 1H), 7.20 (d, 1H), 7.05 (d, 1H), 6.75 (s, br, 1H), 4.30 (m, 2H), 3.70 (m, 2H), 3.35 (m, 4H), 3.30 (s, 3H), 3.01 (m, 2H), 2.75 (m, 5H), 2.35 (s, 3H) | 469 | 4-[(2-fluoro-4-methylphenyl)amino]-7-(2-methoxyethoxy)-6-(4-methylpiperazin-1-yl)cinnoline-3-carbonitrile Method 62 |
| 19 | 4-[(2-Fluoro-5-methylphenyl)amino]-7-(2-methoxyethoxy)-6-(4-methylpiperazin-1-yl)cinnoline-3-carboxamide | 11.05 (s, br, 1H), 8.65 (s, 1H), 8.05 (s, 1H), 7.60 (s, 1H), 7.25-7.10 (m, 3H), 6.81 (s, br, 1H), 4.30 (m, 2H), 3.73 (m, 2H), 3.31 (m, 4H), 3.30 (s, 3H), 3.01 (m, 2H), 2.80 (m, 2H), 2.70 (s, 3H), 2.20 (s, 3H), | 469 | 4-[(2-fluoro-5-methylphenyl)amino]-7-(2-methoxyethoxy)-6-(4-methylpiperazin-1-yl)cinnoline-3-carbonitrile Method 63 |
| 20 | 4-[(2,4-Difluorophenyl)amino]-7-methoxy-6-(4-methylpiperazin-1-yl)cinnoline-3-carboxamide | 11.30 (s, 1H), 8.85 (s, 1H), 7.97 (s, 1H), 7.65 (s, 1H), 7.47 (m, 1H), 7.36 (m, 1H), 7.16 (m, 1H), 6.62 (s, 1H), 4.08 (s, 3H), 2.82 (s, 4H), 2.35 (s, 4H), 2.20 (s, 3H) | 429 | 4-[(2,4-difluorophenyl)amino]-7-methoxy-6-(4-methylpiperazin-1-yl)cinnoline-3-carbonitrile Method 57 |
| 21 | 4-[(3-Chloro-2-fluorophenyl)amino]-7-(2-methoxyethoxy)-6-(4-methylpiperazin-1-yl)cinnoline-3-carboxamide | 11.30 (s, 1H), 8.85 (s, 1H), 7.90 (s, 1H), 7.57 (s, 1H), 7.30 (m, 1H), 7.12 (m, 1H), 7.08 (m, 1H), 6.52 (s, 1H), 4.26 (m, 2H), 3.70 (m, 2H), 3.25 (s, 3H), 2.80 (m, 4H), 2.29 (m, 4H), 2.12 (s, 3H) | 490 | 4-[(3-chloro-2-fluorophenyl)amino]-7-(2-methoxyethoxy)-6-(4-methylpiperazin-1-yl)cinnoline-3-carbonitrile Method 64 |

-continued

| Example | Compound | ¹H NMR (300 MHz) | m/z | Starting Material |
|---|---|---|---|---|
| 22 | 4-[(2-Fluoro-5-methylphenyl)amino]-7-methoxy-6-(4-methylpiperazin-1-yl)cinnoline-3-carboxamide | 11.35 (s, 1H), 8.80 (s, 1H), 7.95 (s, 1H), 7.60 (s, 1H), 7.22 (m, 1H), 7.05 (m, 2H), 6.69 (s, 1H), 4.01 (s, 3H), 2.76 (s, 4H), 2.30 (s, 4H), 2.25 (s, 3H), 2.16 (s, 3H) | 425 | 4-[(2-fluoro-5-methylphenyl)amino]-7-methoxy-6-(4-methylpiperazin-1-yl)cinnoline-3-carbonitrile Method 58 |
| 23 | 4-[(2-Fluoro-5-methylphenyl)amino]-6-(4-isopropylpiperazin-1-yl)-7-methoxycinnoline-3-carboxamide | 11.38 (s, 1H), 8.85 (s, 1H), 8.01 (s, 1H), 7.69 (s, 1H), 7.30 (m, 1H), 7.10 (m, 2H), 6.72 (s, 1H), 4.10 (s, 3H), 2.81 (s, 4H), 2.70 (m, 1H), 2.50 (s, 4H), 2.30 (s, 3H), 1.02 (d, 6H) | 453 | 4-[(2-fluoro-5-methylphenyl)amino]-6-(4-isopropylpiperazin-1-yl)-7-methoxycinnoline-3-carbonitrile Method 59 |
| 24 | 4-[(2,4-Difluorophenyl)amino]-6-(4-isopropylpiperazin-1-yl)-7-(2-methoxyethoxy)cinnoline-3-carboxamide | 11.00 (s, br, 1H), 8.50 (s, 1H), 7.99 (s, 1H), 7.60 (s, 1H), 7.40 (m, 2H), 7.10 (m, 2H), 4.30 (s, 2H), 3.75 (s, 2H), 3.60-3.40 (m, 8H), 3.00 (m, 4H), 1.21 (d, 6H) | 501 | 4-[(2,4-difluorophenyl)amino]-6-(4-isopropylpiperazin-1-yl)-7-(2-methoxyethoxy)cinnoline-3-carbonitrile Method 65 |
| 25 | 7-Ethoxy-4-[(2-fluoro-4-methylphenyl)amino]-6-(4-isopropylpiperazin-1-yl)cinnoline-3-carboxamide | 11.02 (s, br, 1H), 8.59 (s, 1H), 8.05 (s, 1H), 7.55 (s, 1H), 7.29 (m, 1H), 7.20 (d, 1H), 7.08 (d, 1H), 6.80 (s, br, 1H), 4.25 (q, 2H), 3.60 (m, 1H), 3.30 (m, 4H), 2.92 (m, 4H), 2.30 (s, 3H), 1.40 (t, 3H), 1.25 (d, 6H) | 467 | 7-ethoxy-4-[(2-fluoro-4-methylphenyl)amino]-6-(4-isopropylpiperazin-1-yl)cinnoline-3-carbonitrile Method 66 |
| 26 | 4-[(2-Fluoro-4-methylphenyl)amino]-7-methoxy-6-pyridin-4-ylcinnoline-3-carboxamide | 11.64 (s, 1H), 8.84 (s, 1H), 8.54 (d, 2H), 8.00 (s, 1H), 7.78 (s, 1H), 7.58 (m, 3H), 7.29 (m, 2H), 7.15 (m, 1H), 4.01 (s, 3H), 2.37 (s, 3H) | 404 | 4-[(2-fluoro-4-methylphenyl)amino]-7-methoxy-6-pyridin-4-ylcinnoline-3-carbonitrile Method 84 |
| 27 | 7-Ethoxy-4-[(2-fluoro-4-methylphenyl)amino]-6-(4-methyl-1,4-diazepan-1-yl)cinnoline-3-carboxamide | 11.14 (s, 1H), 8.70 (s, 1H), 7.86 (s, 1H), 7.48 (s, 1H), 7.17 (m, 1H), 7.09 (m, 1H), 7.01 (m, 1H), 6.46 (s, 1H), 4.24 (q, 2H), 3.17 (m, 2H), 2.96 (m, 2H), 2.41 (m, 2H), 2.31 (s, 3H), 2.20 (m, 2H), 1.69 (m, 2H), 1.42 (t, 3H) | 453 | 7-ethoxy-4-[(2-fluoro-4-methylphenyl)amino]-6-(4-methyl-1,4-diazepan-1-yl)cinnoline-3-carbonitrile Method 67 |
| 28 | 6-[(3R,5S)-3,5-Dimethylpiperazin-1-yl]-7-ethoxy-4-[(2-fluoro-4-methylphenyl)amino]-cinnoline-3-carboxamide | 11.30 (s, 1H), 8.73 (s, 1H), 7.89 (s, 1H), 7.51 (s, 1H), 7.19 (m, 2H), 7.06 (m, 1H), 6.58 (s, 1H), 4.25 (q, 2H), 3.06 (d, 2H), 2.75 (m, 2H), 2.32 (s, 3H), 1.79 (m, 2H), 1.40 (t, 3H), 0.85 (d, 6H) | 453 | 6-[(3R,5S)-3,5-dimethylpiperazin-1-yl]-7-ethoxy-4-[(2-fluoro-4-methylphenyl)amino]cinnoline-3-carbonitrile Method 68 |
| 29 | 4-[(2-Fluoro-4-methylphenyl)amino]-6-(1-isopropyl-1,2,3,6-tetrahydropyridin-4-yl)-7-methoxycinnoline-3-carboxamide | 12.37 (s, 1H), 10.34 (s, 1H), 8.77 (s, 1H), 8.19 (s, 1H), 7.64 (s, 1H), 7.30 (m, 3H), 7.11 (m, 1H), 5.74 (s, 1H), 4.01 (s, 3H), 3.71 (m, 2H), 3.47 (m, 2H), 2.99 (m, 1H), 2.71 (m, 1H), 2.40 (s, 3H), 2.31 (m, 1H), 1.28 (d, 6H) isolated as HCl salt | 450 | 4-[(2-fluoro-4-methylphenyl)amino]-6-(1-isopropyl-1,2,3,6-tetrahydropyridin-4-yl)-7-methoxycinnoline-3-carbonitrile Method 86 |

-continued

| Example | Compound | ¹H NMR (300 MHz) | m/z | Starting Material |
|---|---|---|---|---|
| 30 | 4-[(2-Fluoro-4-methylphenyl)amino]-7-methoxy-6-[4-(2-methoxyethyl)piperazin-1-yl]cinnoline-3-carboxamide | 11.29 (s, 1H), 8.76 (s, 1H), 7.91 (s, 1H), 7.57 (s, 1H), 7.19 (m, 2H), 7.04 (m, 1H), 6.60 (s, 1H), 3.99 (s, 3H), 3.41 (m, 2H), 3.22 (s, 3H), 2.71 (m, 4H), 2.39 (m, 6H), 2.32 (s, 3H) | 469 | 4-[(2-fluoro-4-methylphenyl)amino]-7-methoxy-6-[4-(2-methoxyethyl)piperazin-1-yl]cinnoline-3-carbonitrile Method 69 |
| 31 | 6-(5,6-Dihydro[1,2,4]triazolo[4,3-a]pyrazin-7(8H)-yl)-4-[(2-fluoro-4-methylphenyl)amino]-7-methoxycinnoline-3-carboxamide | 11.34 (s, 1H), 8.79 (s, 1H), 8.46 (s, 1H), 7.95 (s, 1H), 7.66 (s, 1H), 7.23 (m, 2H), 7.17 (m, 1H), 6.75 (s, 1H), 4.06 (m, 5H), 3.97 (s, 2H), 3.17 (s, 2H), 2.41 (s, 3H) | 449 | 6-(5,6-dihydro[1,2,4]triazolo[4,3-a]pyrazin-7(8H)-yl)-4-[(2-fluoro-4-methylphenyl)amino]-7-methoxycinnoline-3-carbonitrile Method 70 |
| 32 | 4-[(2-Fluoro-4-methylphenyl)amino]-6-(3-hydroxy-2,5,6,8-tetrahydro[1,2,4]triazolo[4,3-a]pyrazin-7(3H)-yl)-7-methoxycinnoline-3-carboxamide | 11.18 (s, 1H), 8.76 (s, 1H), 7.91 (s, 1H), 7.59 (s, 1H), 7.20 (s, 1H), 7.11 (m, 1H), 7.04 (m, 2H), 7.00 (m, 1H), 6.86 (s, 1H), 6.63 (s, 1H), 3.99 (s, 3H), 3.62 (s, 2H), 3.07 (m, 2H), 2.87 (m, 2H), 2.34 (s, 3H) Byproduct from synthesis of Ex 31 | 467 | 6-(5,6-dihydro[1,2,4]triazolo[4,3-a]pyrazin-7(8H)-yl)-4-[(2-fluoro-4-methylphenyl)amino]-7-methoxycinnoline-3-carbonitrile Method 70 |
| 33 | 4-[(2-Fluoro-4-methylphenyl)amino]-6-(hexahydropyrrolo[1,2-a]pyrazin-2(1H)-yl)-7-methoxycinnoline-3-carboxamide | | 451 | 4-[(2-fluoro-4-methylphenyl)amino]-6-(hexahydropyrrolo[1,2-a]pyrazin-2(1H)-yl)-7-methoxycinnoline-3-carbonitrile Method 71 |
| 34 | 4-[(2-Fluoro-4-methylphenyl)amino]-6-[1-(2-hydroxyethyl)-1,2,3,6-tetrahydropyridin-4-yl]-7-methoxycinnoline-3-carboxamide | MeOD 7.49 (s, 1H), 7.41 (s, 2H), 7.28 (m, 2H), 5.73 (s, 1H), 4.12 (s, 3H), 4.04 (m, 1H), 3.95 (t, 2H), 3.84 (m, 1H), 3.70 (m, 1H), 3.37 (m, 3H), 2.75 (m, 1H), 2.54 (m, 1H), 2.51 (s, 3H) | 452 | 6-[1-(2-{[tert-butyl(dimethyl)silyl]oxy}ethyl)-1,2,3,6-tetrahydropyridin-4-yl]-4-[(2-fluoro-4-methylphenyl)amino]-7-methoxycinnoline-3-carbonitrile Method 87 |
| 35 | 4-[(2-Fluoro-4-methylphenyl)amino]-7-methoxy-6-morpholin-4-ylcinnoline-3-carboxamide | 11.33 (s, 1H), 8.77 (s, 1H), 7.92 (s, 1H), 7.59 (s, 1H), 7.18 (m, 2H), 7.04 (m, 1H), 6.62 (s, 1H), 4.00 (s, 3H), 3.60 (m, 4H), 2.68 (m, 4H), 2.31 (s, 3H) | 412 | 4-[(2-fluoro-4-methylphenyl)amino]-7-methoxy-6-morpholin-4-ylcinnoline-3-carbonitrile Method 72 |
| 36 | 6-[(3R,5S)-3,5-Dimethylpiperazin-1-yl]-4-[(2-fluoro-4-methylphenyl)amino]-7-methoxycinnoline-3-carboxamide | 11.33 (s, 1H), 8.76 (s, 1H), 7.90 (s, 1H), 7.55 (s, 1H), 7.21 (m, 2H), 7.06 (m, 1H), 6.61 (s, 1H), 4.07 (br s, 1H), 4.00 (s, 3H), 3.00 (d, 2H), 2.71 (m, 2H), 2.32 (s, 3H), 1.75 (m, 2H), 0.85 (d, 6H) | 439 | 6-[(3R,5S)-3,5-dimethylpiperazin-1-yl]-4-[(2-fluoro-4-methylphenyl)amino]-7-methoxycinnoline-3-carbonitrile Method 73 |
| 37 | 6-[(2R,6S)-2,6-Dimethylmorpholin-4-yl]-4-[(2-fluoro-4-methylphenyl)amino]-7-methoxycinnoline-3-carboxamide | 11.36 (s, 1H), 8.77 (s, 1H), 7.91 (s, 1H), 7.58 (s, 1H), 7.23 (m, 2H), 7.08 (m, 1H), 6.63 (s, 1H), 4.00 (s, 3H), 3.59 (m, 2H), 3.04 (d, 2H), 2.32 (s, 3H), 1.90 (m, 2H), 0.99 (d, 6H) | 440 | 6-[(2R,6S)-2,6-dimethylmorpholin-4-yl]-4-[(2-fluoro-4-methylphenyl)amino]-7-methoxycinnoline-3-carbonitrile Method 74 |

| Example | Compound | ¹H NMR (300 MHz) | m/z | Starting Material |
|---|---|---|---|---|
| 38 | 4-[(2-Fluoro-4-methylphenyl)amino]-6-[4-(2-hydroxyethyl)piperazin-1-yl]-7-methoxycinnoline-3-carboxamide | 11.30 (s, 1H), 8.77 (s, 1H), 7.92 (s, 1H), 7.58 (s, 1H), 7.19 (m, 2H), 7.06 (m, 1H), 6.62 (s, 1H), 4.40 (t, 1H), 4.01 (s, 3H), 3.50 (m, 2H), 2.73 (m, 4H), 2.42 (m, 6H), 2.33 (s, 3H) | 455 | 6-[4-(2-{[tert-butyl(dimethyl)silyl]oxy}-ethyl)piperazin-1-yl]-4-[(2-fluoro-4-methylphenyl)amino]-7-methoxycinnoline-3-carbonitrile Method 75 |
| 39 | 6-[4-(Dimethylamino)piperidin-1-yl]-4-[(2-fluoro-4-methylphenyl)amino]-7-methoxycinnoline-3-carboxamide | 11.28 (s, 1H), 8.76 (s, 1H), 7.91 (s, 1H), 7.57 (s, 1H), 7.18 (m, 2H), 7.05 (m, 1H), 6.63 (s, 1H), 4.01 (s, 3H), 3.22 (m, 2H), 2.34 (s, 3H), 2.28 (m, 2H), 2.15 (s, 6H), 2.10 (m, 1H), 1.63 (m, 2H), 1.38 (m, 2H) | 453 | 6-[4-(dimethylamino)piperidin-1-yl]-4-[(2-fluoro-4-methylphenyl)amino]-7-methoxycinnoline-3-carbonitrile Method 76 |
| 40 | 4-[(2-Fluoro-4-methylphenyl)amino]-7-methoxy-6-(4-methyl-1,4-diazepan-1-yl)cinnoline-3-carboxamide | MeOD 7.33 (s, 1H), 6.94 (m, 3H), 6.43 (s, 1H), 3.93 (s, 3H), 3.12 (m, 2H), 2.85 (m, 2H), 2.58 (m, 2H), 2.49 (m, 2H), 2.26 (s, 3H), 2.23 (s, 3H), 1.75 (m, 2H) | 439 | 4-[(2-fluoro-4-methylphenyl)amino]-7-methoxy-6-(4-methyl-1,4-diazepan-1-yl)cinnoline-3-carbonitrile Method 77 |
| 41 | 6-[(3S)-3-(Dimethylamino)pyrrolidin-1-yl]-4-[(2-fluoro-4-methylphenyl)amino]-7-methoxycinnoline-3-carboxamide | 11.12 (s, 1H), 8.71 (s, 1H), 7.85 (s, 1H), 7.48 (s, 1H), 7.13 (m, 2H), 7.02 (m, 1H), 6.17 (s, 1H), 3.96 (s, 3H), 2.97 (m, 1H), 2.79 (m, 1H), 2.62 (m, 1H), 2.28 (s, 3H), 2.13 (s, 6H), 1.98 (m, 1H), 1.60 (m, 1H). Two protons masked by solvent | 439 | 6-[(3S)-3-(dimethylamino)pyrrolidin-1-yl]-4-[(2-fluoro-4-methylphenyl)amino]-7-methoxycinnoline-3-carbonitrile Method 78 |
| 42 | 4-[(2-Fluoro-4-methylphenyl)amino]-7-methoxy-6-[4-(2,2,2-trifluoroethyl)piperazin-1-yl]cinnoline-3-carboxamide | 11.30 (s, 1H), 8.75 (s, 1H), 7.90 (s, 1H), 7.57 (s, 1H), 7.19 (m, 2H), 7.06 (m, 1H), 6.61 (s, 1H) 3.99 (s, 3H), 3.18 (q, 2H), 2.70 (m, 4H), 2.62 (m, 4H), 2.31 (s, 3H) | 493 | 4-[(2-fluoro-4-methylphenyl)amino]-7-methoxy-6-[4-(2,2,2-trifluoroethyl)piperazin-1-yl]cinnoline-3-carbonitrile Method 79 |
| 43 | 7-Ethoxy-4-[(2-fluoro-4-methylphenyl)amino]-6-[4-(2-hydroxyethyl)piperazin-1-yl]cinnoline-3-carboxamide | CDCl3 11.00 (s, 1H), 8.38 (br s, 1H), 7.55 (s, 1H), 7.07 (m, 1H), 6.93 (m, 2H), 6.75 (m, 1H), 5.59 (br s, 1H), 4.26 (q, 2H), 3.66 (m, 2H), 2.88 (m, 4H), 2.62 (m, 6H), 2.35 (s, 3H), 1.53 (t, 3H) | 469 | 6-[4-(2-{[tert-butyl(dimethyl)silyl]oxy}-ethyl)piperazin-1-yl]-7-ethoxy-4-[(2-fluoro-4-methylphenyl)amino]cinnoline-3-carbonitrile Method 80 |
| 44 | 4-[(2,4-Difluorophenyl)amino]-6-[(3R,5S)-3,5-dimethylpiperazin-1-yl]-7-methoxycinnoline-3-carboxamide | 11.38 (s, 1H), 8.81 (s, 1H), 7.97 (s, 1H), 7.62 (s, 1H), 7.43 (m, 1H), 7.21 (m, 2H), 6.52 (s, 1H), 4.00 (s, 3H), 3.06 (d, 2H), 2.76 (m, 2H), 1.86 (m, 2H), 0.86 (d, 6H) | 443 | 4-[(2,4-difluorophenyl)amino]-6-[(3R,5S)-3,5-dimethylpiperazin-1-yl]-7-methoxycinnoline-3-carbonitrile Method 81 |
| 45 | 4-[(3-Chloro-2-fluorophenyl)amino]-6-[(3R,5S)-3,5-dimethylpiperazin-1-yl]-7-methoxycinnoline-3-carboxamide | 11.34 (s, 1H), 8.79 (s, 1H), 7.94 (s, 1H), 7.59 (s, 1H), 7.45 (m, 2H), 7.17 (m, 1H), 6.55 (s, 1H), 4.01 (s, 3H), 3.04 (d, 2H), 2.77 (m, 2H), 1.80 (m, 2H), 0.88 (d, 6H) | 459 | 4-[(3-chloro-2-fluorophenyl)amino]-6-[(3R,5S)-3,5-dimethylpiperazin-1-yl]-7-methoxycinnoline-3-carbonitrile Method 82 |

-continued

| Example | Compound | ¹H NMR (300 MHz) | m/z | Starting Material |
|---|---|---|---|---|
| 46 | 4-[(2-Fluoro-4-methylphenyl)amino]-7-methoxy-6-piperazin-1-ylcinnoline-3-carboxamide | | 411 | 4-[(2-fluoro-4-methylphenyl)amino]-7-methoxy-6-piperazin-1-ylcinnoline-3-carbonitrile Method 83 |

Example 47

4-[(2-Fluoro-4-methylphenyl)amino]-6-(1-isopropylpiperidin-4-yl)-7-methoxycinnoline-3-carboxamide hydrochloride A solution of 4-(2-fluoro-4-methylphenylamino)-6-(1-isopropyl-1,2,3,6-tetrahydropyridin-4-yl)-7-methoxycinnoline-3-carboxamide (Example 29, 0.250 g, 0.56 mmol) in MeOH (20 ml) with a few drops of c.HCl, was run through an H-Cube apparatus at 1 mL/min using a 20 wt % $Pd(OH)_2$/Carbon cartridge at 10 bar. When the reduction was judged complete by LCMS, the solution was concentrated under reduced pressure to give 0.234 g (86%) product. ¹H NMR: 12.51 (s, 1H), 10.51 (s, 1H), 8.76 (s, 1H), 8.21 (s, 1H), 7.65 (s, 1H), 7.36 (m, 3H), 7.18 (m, 1H), 4.03 (s, 3H), 3.38 (m, 1H), 3.26 (m, 2H), 3.05 (m, 3H), 2.41 (s, 3H), 1.72 (m, 2H), 1.61 (m, 2H), 1.26 (d, 6H); m/z 452.

Example 48

The following example was prepared according to the procedure of Example 47 using the appropriate starting material, with additional purification by reverse phase HPLC.

| Example | Compound | ¹H NMR (300 MHz) | m/z | Starting Material |
|---|---|---|---|---|
| 48 | 4-[(2-Fluoro-4-methylphenyl)amino]-6-[1-(2-hydroxyethyl)piperidin-4-yl]-7-methoxycinnoline-3-carboxamide | MeOD 7.48 (s, 1H), 7.28 (s, 1H), 7.16 (m, 1H), 7.05 (m, 2H), 4.02 (s, 3H), 3.67 (t, 2H), 2.96 (m, 2H), 2.85 (m, 1H), 2.54 (t, 2H), 2.38 (s, 3H), 2.17 (m, 2H), 1.60 (m, 2H), 1.18 (m, 2H) | 454 | 4-[(2-fluoro-4-methylphenyl)amino]-6-[1-(2-hydroxyethyl)-1,2,3,6-tetrahydropyridin-4-yl]-7-methoxycinnoline-3-carboxamide Example 34 |

Example 49

4-[(2-Fluoro-4-methylphenyl)amino]-6-{4-[(2R)-2-hydroxypropanoyl]piperazin-1-yl}-7-methoxycinnoline-3-carboxamide To a solution of 4-(2-fluoro-4-methylphenylamino)-7-methoxy-6-(piperazin-1-yl)cinnoline-3-carboxamide (Example 46, 0.395 g, 0.96 mmol) in $CH_2Cl_2$ (20 mL) and MeOH (5 mL) was added benzotriazol-1-yloxytripyrrolidino-phosphonium hexafluorophosphate (0.551 g, 1.06 mmol), (R)-2-hydroxypropanoic acid (0.079 mL, 1.06 mmol), and N-ethyldiisopropylamine (0.181 mL, 1.06 mmol). After 1 hour, an additional portion of benzotriazol-1-yloxytripyrrolidinophosphonium hexafluorophosphate (1.10 g, 2.12 mmol) was added. After 2 hours, water (100 mL) was added, and the mixture extracted with $CH_2Cl_2$. The organic extract was concentrated under reduced pressure, and the residue purified with silica chromatography (Hex/EtOAc, then with $CH_2Cl_2$/MeOH). The crude product was triturated with $CH_3CN$ and filtered to give 173 mg (37%) yellow solid. ¹H NMR: 11.33 (s, 1H), 8.77 (s, 1H), 7.91 (s, 1H), 7.60 (s, 1H), 7.17 (m, 2H), 7.06 (m, 1H), 6.62 (s, 1H), 4.98 (d, 1H), 4.39 (m, 1H), 4.01 (s, 3H), 3.54 (m, 4H), 2.72 (m, 4H), 2.32 (s, 3H), 1.16 (d, 3H); m/z 484.

Example 50

4-[(2-Fluoro-4-methylphenyl)amino]-7-methoxy-6-[1-(methylsulfonyl)piperidin-4-yl]cinnoline-3-carboxamide To a solution of 4-(2-fluoro-4-methylphenylamino)-7-methoxy-6-(piperidin-4-yl)cinnoline-3-carboxamide (Example 51, 0.1 g, 0.24 mmol) in $CH_2Cl_2$ (2.5 ml) and DMF (2.5 ml) was added N-ethyldiisopropylamine (0.127 ml, 0.73 mmol) and methanesulphonyl chloride (0.021 ml, 0.27 mmol). The reaction mixture was stirred at for 1 hour, diluted with $CH_2Cl_2$ and washed with water. The organic layer was concentrated under reduced pressure and the residue purified by reverse phase chromatography using 0.1% formic acid in water and methanol (50-70%) to give 28 mg (24%) off-white solid. ¹H NMR: 11.56 (s, 1H), 8.78 (s, 1H), 7.94 (s, 1H), 7.61 (s, 1H), 7.29 (m, 1H), 7.21 (m, 1H), 7.11 (m, 2H), 4.01 (s, 3H), 3.51 (m, 2H), 2.91 (m, 1H), 2.84 (s, 3H), 2.74 (m, 2H), 2.35 (s, 3H), 1.63 (m, 2H), 0.97 (m, 2H); m/z 488.

Example 51

4-[(2-Fluoro-4-methylphenyl)amino]-7-methoxy-6-piperidin-4-ylcinnoline-3-carboxamide A solution of 4-(2-fluoro-4-methylphenylamino)-7-methoxy-6-(1,2,3,6-tetrahydropyridin-4-yl)cinnoline-3-carboxamide (Example 52, 0.9 g, 2.21 mmol) in MeOH (44.2 ml) with a few drops of conc. HCl was passed through an H Cube apparatus using a 20 wt % $Pd(OH)_2$/Carbon cartridge, at 10 bar. The solvent was removed under reduced pressure and the residue was purified with silica chromatography CH$_2$Cl$_2$/10% MeOH (1% NH$_4$OH) to give 692 mg (77%) of a light yellow solid. $^1$H NMR: MeOD 7.61 (s, 1H), 7.37 (m, 1H), 7.23 (m, 1H), 7.12 (m, 2H), 4.09 (s, 3H), 3.38 (m, 2H), 3.22 (m, 1H), 3.12 (m, 2H), 2.43 (s, 3H), 1.90 (m, 2H), 1.36 (m, 2H); m/z 410.

Example 52

4-[(2-Fluoro-4-methylphenyl)amino]-7-methoxy-6-(1,2,3,6-tetrahydropyridin-4-yl)cinnoline-3-carboxamide A solution of tert-butyl 4-(3-carbamoyl-4-(2-fluoro-4-methylphenylamino)-7-methoxycinnolin-6-yl)-5,6-dihydropyridine-1(2H)-carboxylate (Example 53, 1.5 g, 2.96 mmol) in CH$_2$Cl$_2$ (11.84 mL) and trifluoroacetic acid (11.84 mL, 153.68 mmol) was stirred for 16 hours, concentrated under reduced pressure, and the residue purified with silica chromatography CH$_2$Cl$_2$/5% MeOH (1% NH$_4$OH) to give 960 mg (80%) product. m/z 408.

Example 53 tert-Butyl 4-{3-(aminocarbonyl)-4-[(2-fluoro-4-methylphenyl)amino]-7-methoxycinnolin-6-yl}-3,6-dihydropyridine-1(2H)-carboxylate A mixture of 6-bromo-4-(2-fluoro-4-methylphenylamino)-7-methoxycinnoline-3-carboxamide hydrochloride (Example 54, 1.40 g, 3.169 mmol), tert-butyl 4-(4,4,5,5-tetramethyl-1,3,2-dioxaborolan-2-yl)-5,6-dihydropyridine-1(2H)-carboxylate (1.47 g, 4.75 mmol), tripotassium phosphate (2.018 g, 9.51 mmol), dicyclohexyl(2',6'-dimethoxybiphenyl-2-yl)phosphine (0.260 g, 0.63 mmol) and tris(dibenzylideneacetone)dipalladium(0) (0.29 g, 0.32 mmol) in n-butanol (4.53 ml) and water (1.81 ml) was stirred under N$_2$ (g) at 100° C. overnight. The reaction mixture was cooled, concentrated under reduced pressure and the residue purified with silica chromatography (CH$_2$Cl$_2$/MeOH) to give 1.54 g (96%) of a light brown solid. $^1$H NMR: 11.54 (s, 1H), 8.79 (s, 1H), 7.94 (s, 1H), 7.62 (s, 1H), 7.25 (m, 2H), 7.08 (m, 2H), 5.56 (s, 1H), 3.97 (s, 3H), 3.82 (m, 2H), 3.37 (m, 2H), 2.35 (s, 3H), 2.14 (m, 2H), 1.41 (s, 6H), 1.06 (s, 9H); m/z 508.

Example 54

6-Bromo-4-[(2-fluoro-4-methylphenyl)amino]-7-methoxycinnoline-3-carboxamide hydrochloride To a suspension of 6-bromo-4-chloro-7-methoxycinnoline-3-carboxamide (Method 21, 8.89 g, 28.09 mmol) in ethanol (70 ml) was added 2-fluoro-4-methylaniline (3.49 ml, 30.89 mmol) and acetic acid (0.016 ml, 0.28 mmol). The reaction mixture was stirred at 80° C. for 1 hour, cooled, and filtered. The solid material was washed with ethanol and dried to give 9.16 g (74%) of a brown solid, assumed to be the HCl salt. $^1$H NMR: 12.15 (s, 1H), 8.79 (s, 1H), 8.13 (s, 1H), 7.73 (s, 1H), 7.66 (s, 1H), 7.33 (m, 2H), 7.12 (m, 1H), 4.07 (s, 3H), 2.38 (s, 3H); m/z 406.

Preparation of Starting Materials

Method 1

1-{4,5-Dimethoxy-2-[(E)-pyrrolidin-1-yldiazenyl]phenyl}ethanone

To a 100 mL round bottom flask charged with a magnetic stir bar and 1-(2-amino-4,5-dimethoxyphenyl)ethanone (1.23 g, 6.29 mmol) was added water (4 mL). The mixture was cooled to 0° C. with an ice bath and concentrated aqueous HCl (1.95 mL) was added to the reaction mixture. With efficient stirring, a solution of sodium nitrite (0.434 g, 6.9 mmol) in water (3 mL) was added to the reaction mixture via Pasteur pipette. The reaction was allowed to stir for 5 minutes at this temperature followed by the slow addition of a solution of pyrrolidine (0.447 g, 6.30 mmol) in 50 mL of 0.4 N aqueous potassium hydroxide. The reaction was allowed to stir at this temperature for 0.5 h before being poured into a separatory funnel and extracted with DCM (2×100 mL). The combined organic extract was dried with MgSO$_4$, filtered, and concentrated in vacuo to yield the crude product which was purified on 80 g of silica using hexanes/EtOAc (1:1) as eluent to give 1.49 g (85%) of the title compound as a brown solid. $^1$H NMR: 7.12 (s, 1H), 7.01 (s, 1H), 3.92 (m, 2H), 3.80 (s, 3H), 3.75 (s, 3H), 3.58 (m, 2H), 2.60 (s, 3H), 2.00 (M, 4H); m/z: 278.

Method 2

The following intermediate was prepared according to the procedure in Method 1 using the appropriate starting material.

| Method | Compound | $^1$H NMR (300 MHz) | m/z | Starting Material |
|---|---|---|---|---|
| 2 | 1-{5-Bromo-4-ethoxy-2-[(E)-pyrrolidin-1-yldiazenyl]phenyl}ethanone | 7.79 (s, 1H), 7.11 (s, 1H), 4.20 (q, 2H), 4.05 (m, 2H), 3.69 (m, 2H), 2.62 (s, 3H), 2.07 (m, 4H), 1.45 (t, 3H) | 341 | 1-(2-amino-5-bromo-4-ethoxyphenyl)ethanone (Method 46) |

Method 3

Ethyl 3-{4,5-dimethoxy-2-[(E)-pyrrolidin-1-yldiazenyl]phenyl}-3-oxopropanoate sodium salt To a 250 mL three-necked flask charged with a magnetic stir bar and anhydrous THF (55 mL) was added sodium hydride (1.73 g, 43.3 mmol) and freshly distilled diethyl carbonate (1.28 g, 10.83 mmol). The reaction mixture was brought to reflux and a solution of 1-{4,5-dimethoxy-2-[(E)-pyrrolidin-1-yldiazenyl]phenyl}ethanone (3.0 g, 10.83 mmol) (Method 1) in anhydrous THF (25 mL) was added dropwise via an addition funnel. The mixture was refluxed for an additional 8 h before being allowed to cool to rt. The light yellow precipitate was isolated via vacuum filtration using a Buchner funnel, washed with diethyl ether (~2×100 mL), collected, and dried in vacuo to yield 4.03 g (99%) of the title compound as its sodium salt which was used without further purification. $^1$H NMR: 7.10 (s, 1H), 6.71 (s, 1H), 4.75 (s, 1H), 3.85 (m, 2H), 3.71 (s, 3H), 3.70 (s, 3H), 3.62 (m, 2H), 3.44 (m, 2H), 1.96 (M, 4H), 1.05 (m, 3H); m/z: 350.

Method 4

The following intermediate was prepared according to the procedure in Method 3 using the appropriate starting materials.

| Method | Compound | $^1$H NMR (300 MHz) | m/z | Starting Material |
|---|---|---|---|---|
| 4 | Ethyl 3-{5-bromo-4-ethoxy-2-[(E)-pyrrolidin-1-yldiazenyl]phenyl}-3-oxopropanoate | 7.66 (s, 1H), 6.75 (s, 1H), 4.80 (s, 1H), 4.05-3.30 (m, 8H), 1.32 (t, 2H), 1.02 (m, 8H) | 413 | 1-{5-bromo-4-ethoxy-2-[(E)-pyrrolidin-1-yldiazenyl]-phenyl}-ethanone (Method 2) |

Method 5

Ethyl 6,7-dimethoxy-4-oxo-1,4-dihydrocinnoline-3-carboxylate

To a 100 mL round bottom flask charged with a magnetic stir bar was added TFA (30 mL). The flask was cooled to 0° C. in an ice bath and ethyl 3-{4,5-dimethoxy-2-[(E)-pyrrolidin-1-yldiazenyl]phenyl}-3-oxopropanoate sodium salt (4.03 g, 10.83 mmol) (Method 3) was added to the reaction mixture in portions over 10 minutes. The mixture was stirred at this temperature for an additional 2 h before being poured over 0° C. ice-water (~300 mL). The desired product precipitated from the mixture and was collected via vacuum filtration using a Buchner funnel. The solid was rinsed with water (1×100 mL) and diethyl ether (1×100 mL) to yield 1.55 g (51%) of the title compound as an off white solid that was used without further purification. $^1$H NMR: 13.70 (s, NH, 1H), 7.39 (s, 1H), 7.00 (s, 1H), 4.30 (q, 2H), 3.95 (s, 3H), 3.89 (s, 3H), 1.30 (t, 3H); m/z 279.

Method 6

The following intermediate was prepared according to the procedure in Method 5 using the appropriate starting material.

| Method | Compound | $^1$H NMR (300 MHz) | m/z | Starting Material |
|---|---|---|---|---|
| 6 | Ethyl 6-bromo-7-ethoxy-4-oxo-1,4-dihydrocinnoline-3-carboxylate | 13.76 (s, 1H), 8.20 (s, 1H), 7.08 (s, 1H), 4.30 (m, 4H), 1.48 (t, 3H), 1.27 (t, 3H) | 342 | ethyl 3-{5-bromo-4-ethoxy-2-[(E)-pyrrolidin-1-yldiazenyl]phenyl}-3-oxopropanoate (Method 4) |

Method 7

Ethyl 4-chloro-6,7-dimethoxycinnoline-3-carboxylate

To a 50 mL round bottom flask charged with a magnetic stir bar and ethyl 6,7-dimethoxy-4-oxo-1,4-dihydrocinnoline-3-carboxylate (1.00 g, 3.6 mmol) (Method 5) was added phosphorous oxychloride (15 mL). The reaction flask was fitted with a reflux condenser and heated to reflux for 2 h before being allowed to cool to rt. The crude reaction mixture was concentrated in vacuo, and the residue was treated with aqueous NaHCO$_3$ (~25 mL). The crude product precipitated from solution and was collected via vacuum filtration using a Buchner funnel. The solid was washed water (1×100 mL) and diethyl ether (1×100 mL) to yield 0.941 g (88%) of the title compound as a light brown solid that was used without further purification. $^1$H NMR: 7.98 (s, 1H), 7.50 (s, 1H), 4.55 (q, 2H), 4.13 (s, 6H), 1.45 (t, 3H); m/z 298.

Method 8

The following intermediate was prepared according to the procedure in Method 7 using the appropriate starting material.

| Method | Compound | m/z | Starting Material |
|---|---|---|---|
| 8 | Ethyl 6-bromo-4-chloro-7-ethoxycinnoline-3-carboxylate | 361 | ethyl 6-bromo-7-ethoxy-4-oxo-1,4-dihydrocinnoline-3-carboxylate (Method 6) |

Method 9

2-Bromo-5-nitrophenol

To a 500 mL round bottom flask charged with 2-bromo-5-nitroanisole (11.0 g, 47 mmol) was added 100 mL of anhydrous DCM. Aluminum chloride (25 g, 150 mmol) was then added to the reaction mixture. The resulting suspension was heated overnight under nitrogen at 50° C. The reaction was allowed to cool to rt, poured over ice, and acidified to pH 4 with the addition of aqueous 10% HCl. The resulting mixture was filtered through a bed of Celite and the filtrate was transferred to a separatory funnel. The aqueous phase was extracted with methylene chloride (~2×200 mL). The combined organic phase was dried over Na$_2$SO$_4$ and conc in vacuo giving the crude title compound which was purified by silica gel chromatography (330 g) using EtOAc/hexanes (1:1) as eluent to afford the title compound (8.0 g, 78%) m/z: 217.

Method 10

1-Bromo-2-(2-methoxyethoxy)-4-nitrobenzene

To a solution of 2-bromo-5-nitrophenol (7.24 g, 33.2 mmol) (Method 9) in anhydrous DMF was added 2-methoxy-1-bromoethane (6.92 g, 49.8 mmol) and a catalytic amount of potassium iodide (~100 mg). The reaction was heated at 70° C. for 4 h before being allowed to cool to rt. The reaction was then poured into a separatory funnel and partitioned between EtOAc (~250 mL) and water (~250 mL). The organic phase was dried over Na$_2$SO$_4$ and conc in vacuo giving the crude title compound which was taken up in a minimum volume of warm EtOAc. The resulting solution was cooled in an ice bath and hexanes were slowly added to induce crystallization. The resulting precipitate was isolated via vacuum filtration through a fritted funnel and air dried to give pure title compound (8.3 g, 91%). $^1$H NMR: (300 MHz) 7.87-7.92 (m, 2H), 7.76 (dd, 1H), 4.35 (t, 2H), 3.73 (t, 2H), 3.35 (s, 3H).

Method 11

4-Bromo-3-(2-methoxyethoxy)aniline

An open 250 mL round bottom flask was charged with 1-bromo-2-(2-methoxyethoxy)-4-nitrobenzene (Method 10) (5 g, 18.11 mmol), 5 wt % FeCl$_3$ on SiO$_2$ (17.6 g, 5.43 mmol), activated carbon (10 g), and 100 mL MeOH. This resulting mixture was heated with stirring to 80° C. Hydrazine monohydrate (10.6 mL, 217 mmol) was then carefully added to the reaction mixture. After complete addition of the hydrazine monohydrate, the reaction mixture was stirred at 80° C. for an additional 40 min. The reaction was then allowed to cool to rt and filtered through a bed of Celite. The filter cake was washed with MeOH (~150 mL) and EtOAc (~150 mL). The resulting filtrate was conc in vacuo to give the title compound which was used without further purification (3.16 g, 71%) m/z: 247.

Method 12

2-[(4-Bromo-3-methoxyphenyl)diazenyl]-2-cyanoacetamide

Sodium nitrite (8.54 g, 123.7 mmol) dissolved in water (100 ml) was added to an ice-cold suspension of 4-bromo-3-methoxyaniline (25 g, 123.7 mmol) in concentrated HCl (46 ml, 1514 mmol) and water (100 ml). After stirring for 10 minutes, 2-cyanoacetamide (10.40 g, 123.7 mmol) and sodium acetate trihydrate (84 g, 617 mmol) in water (1.8 L) was added and the reaction was allowed to stir overnight. The resulting solid was collected by filtration, washed with water, dried, giving an orange solid which was refluxed in 1.4 L of ethanol for 30 min. The mixture was cooled to room temperature, the solid was collected by filtration, washed with ethanol (100 ml×3), and dried to yield the title compound as a yellow solid (34.4 g, 94%). $^1$H NMR: 11.70 (s, 1H), 7.90 (s, 1H), 7.50 (m, 2H), 7.35 (s, 1H), 7.20 (d, 1H), 3.90 (s, 3H); m/z: 296.

Methods 13-14

The following intermediates were prepared according to the procedure in Method 12 using the appropriate starting material.

| Method | Compound | m/z | Starting Material |
| --- | --- | --- | --- |
| 13 | 2-[(E)-(4-Bromo-3-ethoxyphenyl)diazenyl]-2-cyanoacetamide | 312 | 4-bromo-3-ethoxyaniline |
| 14 | 2-{(E)-[4-Bromo-3-(2-methoxyethoxy)phenyl]diazenyl}-2-cyanoacetamide | 342 | 4-bromo-3-(2-methoxyethoxy)-aniline Method 11 |

Method 15

4-Amino-6-bromo-7-methoxycinnoline-3-carboxamide

To a mixture of 2-((4-bromo-3-methoxyphenyl)diazenyl)-2-cyanoacetamide (Method 12) (34.4 g, 115.8 mmol) in toluene (250 ml) under N$_2$ was added TiCl$_4$ (51.1 ml, 463 mmol). The reaction mixture was stirred at reflux for 4 hours before being allowed to cool to room temperature. The reaction mixture was carefully poured over an ice cold solution of 3N HCl (~600 ml), the mixture was then allowed to warm to rt, and was then stirred at 90° C. for 10 minutes. A precipitate formed which was collected via vacuum filtration, washed with water (~200 mL), ethanol (~200 mL), ether (~200 mL), and dried in vacuo to yield the title compound as a brown solid which was used without further purification (30.0 g, 87%). $^1$H NMR: 10.30 (s, br, 1H), 9.95 (s, br, 1H), 9.15 (s, 1H), 8.55 (s, 1H), 8.09 (s, 1H), 7.68 (s, 1H), 4.15 (s, 3H); m/z 298.

Methods 16-17

The following intermediates were prepared according to the procedure in Method 15 using the appropriate starting material.

| Method | Compound | m/z | Starting Material |
| --- | --- | --- | --- |
| 16 | 4-Amino-6-bromo-7-ethoxycinnoline-3-carboxamide | 312 | 2-[(E)-(4-bromo-3-ethoxyphenyl)diazenyl]-2-cyanoacetamide Method 13 |
| 17 | 4-Amino-6-bromo-7-(2-methoxyethoxy)cinnoline-3-carboxamide | 342 | 2-{(E)-[4-bromo-3-(2-methoxyethoxy)-phenyl]diazenyl}-2-cyanoacetamide Method 14 |

Method 18

6-Bromo-4-hydroxy-7-methoxycinnoline-3-carboxylic acid

A 1 L flask was charged with 4-amino-6-bromo-7-methoxycinnoline-3-carboxamide (Method 15) (30 g, 101 mmol) and ethanol (650 ml). A suspension of potassium hydroxide (100 g, 1782 mmol) in water (350 ml) was added to the reaction and the mixture was stirred at reflux for 9 days. The reaction was then cooled and filtered through a pad of Celite which was washed with water (~250 mL). The resulting filtrate was conc. in vacuo to remove the ethanol and the resulting aqueous solution was acidified with conc. HCl to pH 3. A precipitate formed which was collected by vacuum filtration. The resulting solid was suspended in 1.4 L of ethanol, heated to 75° C. for 15 minutes, and cooled to room temperature which provided the crude precipitate which was collected by vacuum filtration. The filter cake was washed with ethanol (~200 mL) and diethyl ether (~200 mL) to yield the title compound as a brown solid which was used without further purification (26.0 g, 86%). $^1$HNMR: 14.60 (m, br, 2H), 8.35 (s, 1H), 7.23 (s, 1H), 4.08 (s, 3H); m/z: 310.

Methods 19-20

The following intermediates were prepared according to the procedure in Method 18 using the appropriate starting material.

| Method | Compound | m/z | Starting Material |
| --- | --- | --- | --- |
| 19 | 6-Bromo-7-ethoxy-4-hydroxycinnoline-3-carboxylic acid | 314 | 4-amino-6-bromo-7-ethoxycinnoline-3-carboxamide Method 16 |

-continued

| Method | Compound | m/z | Starting Material |
|---|---|---|---|
| 20 | 6-Bromo-4-hydroxy-7-(2-methoxyethoxy)cinnoline-3-carboxylic acid | 342 (M − H)⁻ | 4-amino-6-bromo-7-(2-methoxyethoxy)-cinnoline-3-carboxamide Method 17 |

Method 21

6-Bromo-4-chloro-7-methoxycinnoline-3-carboxamide

To a 1 L round bottom flask charged with 6-bromo-4-hydroxy-7-methoxycinnoline-3-carboxylic acid (Method 18) (14 g, 46.8 mmol) was added $SOCl_2$ (342 ml) and DMF (1 ml). The resulting mixture was heated to reflux for 4 hours before being cooled to rt. The reaction mixture was conc. in vacuo to yield a residue which was suspended in acetone (~400 ml). The suspension was cooled to 0° C. in an ice bath and conc. aqueous ammonia (50 ml, 1284 mmol) was added drop wise via an addition funnel and the resulting mixture was allowed to stir at 0° C. for an additional 15 minutes. A precipitate formed which was collected via vacuum filtration. The filter cake was washed with water (3×100 mL), acetone (3×50 mL), collected, and dried in vacuo to yield the title compound as an off white solid (14.00 g, 94%) which was used without further purification. $^1$H NMR: 8.55 (s, 1H), 8.40 (s, 1H), 8.05 (m, 2H), 4.10 (s, 3H); m/z: 317.

Methods 22-23

The following intermediates were prepared according to the procedure in Method 21 using the appropriate starting material.

| Method | Compound | m/z | Starting Material |
|---|---|---|---|
| 22 | 6-Bromo-4-chloro-7-ethoxycinnoline-3-carboxamide | 331 | 6-bromo-7-ethoxy-4-hydroxycinnoline-3-carboxylic acid Method 19 |
| 23 | 6-Bromo-4-chloro-7-(2-methoxyethoxy)cinnoline-3-carboxamide | 361 | 6-bromo-4-hydroxy-7-(2-methoxyethoxy)cinnoline-3-carboxylic acid Method 20 |

Method 24

6-Bromo-4-chloro-7-methoxycinnoline-3-carbonitrile

To a suspension of 6-bromo-4-chloro-7-methoxycinnoline-3-carboxamide (Method 21) (12 g, 37.9 mmol) in DCM (400 ml) was added $POCl_3$ (200 ml). Triethylamine (15 ml) was then added carefully to the mixture which was stirred at reflux for 7 h. The reaction was then allowed to cool to rt and conc. in vacuo. The crude residue was then carefully treated with sat'd aqueous $NaHCO_3$ at 0° C. A precipitate formed which was collected via vacuum filtration. The filter cake washed with water (~100 mL), collected, and dried in vacuo to provide the title compound as a grey solid (9.80 g, 87%) which was used without further purification. $^1$H NMR: 8.71 (s, 1H), 8.29 (s, 1H), 4.30 (s, 3H); m/z: 299.

Methods 25-26

The following intermediates were prepared according to the procedure in Method 24 using the appropriate starting material.

| Method | Compound | m/z | Starting Material |
|---|---|---|---|
| 25 | 6-Bromo-4-chloro-7-ethoxycinnoline-3-carbonitrile | 313 | 6-bromo-4-chloro-7-ethoxycinnoline-3-carboxamide Method 22 |
| 26 | 6-Bromo-4-chloro-7-(2-methoxyethoxy)cinnoline-3-carbonitrile | 343 | 6-bromo-4-chloro-7-(2-methoxyethoxy)-cinnoline-3-carboxamide Method 23 |

Method 27

Ethyl 4-[(2,4-difluorophenyl)amino]-6,7-dimethoxycinnoline-3-carboxylate

To a 50 mL round bottom flask charged with a magnetic stir bar and ethyl 4-chloro-6,7-dimethoxycinnoline-3-carboxylate (0.200 g, 0.675 mmol) (Method 7) was added anhydrous ethanol (10 mL), 2,4-difluoroaniline (0.087 g, 0.675 mmol), and glacial acetic acid (~100 μL). The reaction mixture was then heated to 75° C. for 1 h, cooled to rt, and diluted with concentrated aqueous ammonia (~5 mL). The crude product precipitated from this reaction mixture and was collected via vacuum filtration using a Buchner funnel. The solid was washed water (1×100 mL) and diethyl ether (1×100 mL) to yield the crude product which was purified on 40 g silica using EtOAc as eluent providing 0.231 g (88%) of the title compound as a yellow solid. $^1$H NMR: 9.25 (s, 1H), 7.70 (s, 1H), 7.50 (s, 1H), 7.40 (m, 1H), 7.30 (m, 1H), 7.10 (m, 1H), 4.02 (s, 3H), 3.95 (q, 2H), 3.85 (s, 3H), 1.20 (t, 3H); m/z 390.

Methods 28-45

The following intermediates were prepared according to the procedure in Method 27 using the appropriate starting materials.

| Method | Compound | $^1$H NMR (300 MHz) | m/z | Starting Material |
|---|---|---|---|---|
| 28 | Ethyl 6-bromo-7-ethoxy-4-[(2-fluoro-5-methylphenyl)amino]cinnoline-3-carboxylate | 10.47 (s, 1H), 7.72 (s, 2H), 7.06 (d, 2H), 6.99 (s, 1H), 4.57 (q, 2H), 4.30 (q, 2H), 2.29 (s, 3H), 1.53 (m, 6H) | 449 | ethyl 6-bromo-4-chloro-7-ethoxycinnoline-3-carboxylate (Method 8) and 2-fluoro-5-methylaniline |

| Method | Compound | ¹H NMR (300 MHz) | m/z | Starting Material |
|---|---|---|---|---|
| 29 | Ethyl 4-[(2-fluoro-4-methylphenyl)amino]-6,7-dimethoxycinnoline-3-carboxylate | 9.29 (s, 1H), 7.70 (s, 1H), 7.40 (s, 1H), 7.18-7.09 (m, 2H), 7.00 (d, 1H), 4.00 (s, 3H), 3.95 (q, 2H), 3.75 (s, 3H), 2.30 (s, 3H), 1.20 (t, 3H) | 386 | ethyl 4-chloro-6,7-dimethoxycinnoline-3-carboxylate (Method 7) and 2-fluoro-4-methylaniline |
| 30 | Ethyl 4-[(3-chloro-2-fluorophenyl)amino]-6,7-dimethoxycinnoline-3-carboxylate | 9.30 (s, 1H), 7.74 (s, 1H), 7.59 (s, 1H), 7.35 (t, 1H), 7.15 (t, 1H), 7.10 (t, 1H), 4.05 (s, 3H), 3.90-3.87 (m, 5H), 1.15 (t, 3H) | 407 | ethyl 4-chloro-6,7-dimethoxycinnoline-3-carboxylate (Method 7) and 2-fluoro-3-chloroaniline |
| 31 | Ethyl 4-[(2-fluoro-5-methylphenyl)amino]-6,7-dimethoxycinnoline-3-carboxylate | 9.25 (s, 1H), 7.70 (s, 1H), 7.52 (s, 1H), 7.20 (t, 1H), 7.00 (m, 2H), 4.05 (s, 3H), 3.90 (q, 2H), 3.80 (s, 3H), 2.22 (s, 3H), 1.19 (t, 3H) | 386 | ethyl 4-chloro-6,7-dimethoxycinnoline-3-carboxylate (Method 7) and 2-fluoro-5-methylaniline |
| 32 | Ethyl 4-[(2,3-dichlorophenyl)amino]-6,7-dimethoxycinnoline-3-carboxylate | 9.40 (s, 1H), 7.78 (s, 1H), 7.41 (d, 1H), 7.26 (m, 2H), 7.00 (d, 1H), 4.05 (m, 5H), 3.79 (s, 3H), 1.20 (t, 3H) | 423 | ethyl 4-chloro-6,7-dimethoxycinnoline-3-carboxylate (Method 7) and 2,3-dichloroaniline |
| 33 | Ethyl 6-bromo-4-[(2,4-difluorophenyl)amino]-7-ethoxycinnoline-3-carboxylate | 9.25 (s, 1H), 7.70 (s, 1H), 7.50 (s, 1H), 7.40 (m, 1H), 7.30 (m, 1H), 7.10 (m, 1H), 4.02 (s, 3H), 3.95 (q, 2H), 3.85 (s, 3H), 1.20 (t, 3H) | 453 | ethyl 6-bromo-4-chloro-7-ethoxycinnoline-3-carboxylate (Method 8) and 2,4-difluoroaniline |
| 34 | Ethyl 6-bromo-4-[(2,3-dichlorophenyl)amino]-7-ethoxy-cinnoline-3-carboxylate | | 486 | ethyl 6-bromo-4-chloro-7-ethoxycinnoline-3-carboxylate (Method 8) and 2,3-dichloroaniline |
| 35 | Ethyl 6-bromo-4-[(3-chloro-2-fluoro-phenyl)amino]-7-ethoxy-cinnoline-3-carboxylate | | 470 | ethyl 6-bromo-4-chloro-7-ethoxycinnoline-3-carboxylate (Method 8) and 2-fluoro-3-chloroaniline |
| 36 | Ethyl 6-bromo-7-ethoxy-4-[(2-fluoro-4-methyl-phenyl)amino]cinnoline-3-carboxylate | 9.58 (s, 1H), 8.56 (s, 1H), 7.77 (s, 1H), 7.17 (d, 2H), 7.02 (s, 1H), 4.36 (q, 2H), 3.88 (q, 2H), 2.32 (s, 3H), 1.45 (t, 3H), 1.16 (t, 3H) | 449 | ethyl 6-bromo-4-chloro-7-ethoxycinnoline-3-carboxylate (Method 8) and 2-fluoro-4-methylaniline |
| 37 | 6-Bromo-4-[(3-chloro-2-fluorophenyl)amino]-7-methoxycinnoline-3-carbonitrile | | 408 | 6-bromo-4-chloro-7-methoxycinnoline-3-carbonitrile Method 24 and 3-chloro-2-fluoroaniline |
| 38 | 6-Bromo-4-[(2-fluoro-4-methylphenyl)amino]-7-methoxycinnoline-3-carbonitrile | | 388 | 6-bromo-4-chloro-7-methoxycinnoline-3-carbonitrile Method 24 and 2-fluoro-4-methylaniline |
| 39 | 6-Bromo-4-[(2,4-difluorophenyl)amino]-7-methoxycinnoline-3-carbonitrile | | 392 | 6-bromo-4-chloro-7-methoxycinnoline-3-carbonitrile Method 24 and 2,4-difluoroaniline |

-continued

| Method | Compound | 1H NMR (300 MHz) | m/z | Starting Material |
|---|---|---|---|---|
| 40 | 6-Bromo-4-[(2-fluoro-5-methylphenyl)amino]-7-methoxycinnoline-3-carbonitrile | | 388 | 6-bromo-4-chloro-7-methoxycinnoline-3-carbonitrile Method 24 and 2-fluoro-5-methylaniline |
| 41 | 6-Bromo-4-[(2,4-difluorophenyl)amino]-7-(2-methoxyethoxy)cinnoline-3-carbonitrile | | 436 | 6-bromo-4-chloro-7-(2-methoxyethoxy)cinnoline-3-carbonitrile Method 26 and 2,4-difluoroaniline |
| 42 | 6-Bromo-4-[(2-fluoro-4-methylphenyl)amino]-7-(2-methoxyethoxy)cinnoline-3-carbonitrile | | 432 | 6-bromo-4-chloro-7-(2-methoxyethoxy)cinnoline-3-carbonitrile Method 26 and 2-fluoro-4-methylaniline |
| 43 | 6-Bromo-4-[(2-fluoro-5-methylphenyl)amino]-7-(2-methoxyethoxy)cinnoline-3-carbonitrile | | 432 | 6-bromo-4-chloro-7-(2-methoxyethoxy)cinnoline-3-carbonitrile Method 26 and 2-fluoro-5-methylaniline |
| 44 | 6-Bromo-4-[(3-chloro-2-fluorophenyl)amino]-7-(2-methoxyethoxy)cinnoline-3-carbonitrile | | 453 | 6-bromo-4-chloro-7-(2-methoxyethoxy)cinnoline-3-carbonitrile Method 26 and 3-chloro-2-fluoroaniline |
| 45 | 6-Bromo-7-ethoxy-4-[(2-fluoro-4-methylphenyl)amino]cinnoline-3-carbonitrile | | 402 | 6-bromo-4-chloro-7-ethoxycinnoline-3-carbonitrile Method 25 and 2-fluoro-4-methylaniline |

The intermediates described in Methods 37-45 can also be prepared in two steps from the intermediates of Methods 21-23, using the aniline addition procedure described for Example 54, followed by the conversion of the amide to the nitrile described in Method 24.

Method 46

1-(2-Amino-5-bromo-4-ethoxyphenyl)ethanone

A 1 L three-necked flask fitted with a reflux condenser and an addition funnel was charged with a magnetic stir bar, 4-bromo-3-ethoxyaniline hydrochloride (25 g, 100 mmol), and anhydrous toluene (300 mL). The reaction mixture was cooled to 0° C. and 100 mL a 1 M solution of boron trichloride in DCM was added to the reaction dropwise via addition funnel. After the addition of the boron trichloride was complete, acetonitrile (6.56 mL, 125 mmol) was added followed by dropwise addition of 110 mL of a 1M solution of $TiCl_4$ in DCM. The resulting heterogenous reaction mixture was heated to reflux for 16 h before being allowed to cool to rt. The crude reaction mixture was carefully poured over 2 M $HCl_{(aq)}$ (~250 mL) and the reaction mixture was warmed to 80° C. for 1 h. After cooling to rt the pH of the reaction mixture was adjusted to 6 by the careful addition of 2 N $NaOH_{(aq)}$. The solids were filtered and filtrate was extracted with EtOAc (2×1000 mL). The combined organic extract was dried with $MgSO_4$, filtered, and concentrated in vacuo to yield the crude product as a dark oil. MeOH (~100 mL) was added to the crude oil and the desired product precipitated and was collected via vacuum filtration using a Buchner funnel to yield 10.9 g (42%) of the title compound as a brown solid. m/z 259.

Method 47

Ethyl 7-ethoxy-4-[(2-fluoro-5-methylphenyl)amino]-6-(4-methylpiperazin-1-yl)cinnoline-3-carboxylate To a 50 mL round bottom flask charged with a magnetic stir bar and ethyl 6-bromo-7-ethoxy-4-[(2-fluoro-5-methylphenyl)amino]cinnoline-3-carboxylate (0.100 g, 0.223 mmol) (Method 28) was added 2.5 mL of anhydrous dimethylacetamide. $Pd_2(dba)_3$ (50 mg, 0.55 mmol), racemic BINAP (70 mg, 0.11 mmol), cesium carbonate (150 mg, 0.45 mmol), and 1-methylpiperazine (0.334 mmol) were added to the reaction. The mixture was heated to 90° C. for 4 h before being cooled to rt and filtered though a pad of diatomaceous earth. The filtrate was concentrated in vacuo giving the crude product which was purified on 12 g silica using EtOAc/MeOH (4:1) as eluent yielding 0.033 g (32%) of the title compound as a yellow solid. m/z 468.

Methods 48-83

The following intermediates were prepared according to the procedure in Method 47 using the appropriate starting materials. Some intermediates were prepared using sodium tert-butoxide in place of cesium carbonate, or 2-dicyclohexylphosphino-2',4',6'-tri-iso-propyl-1,1'-biphenyl (XPHOS) in place of BINAP.

| Method | Compound | m/z | Starting Material |
|---|---|---|---|
| 48 | Ethyl 4-[(2,4-difluorophenyl)amino]-7-ethoxy-6-(4-methylpiperazin-1-yl)cinnoline-3-carboxylate | 472 | ethyl 6-bromo-4-[(2,4-difluorophenyl)amino]-7-ethoxycinnoline-3-carboxylate (Method 33) |
| 49 | Ethyl 4-[(2,3-dichlorophenyl)amino]-7-ethoxy-6-(4-methylpiperazin-1-yl)cinnoline-3-carboxylate | 505 | ethyl 6-bromo-4-[(2,3-dichlorophenyl)amino]-7-ethoxy-cinnoline-3-carboxylate (Method 34) |
| 50 | Ethyl 4-[(3-chloro-2-fluoro-phenyl)amino]-7-ethoxy-6-(4-methylpiperazin-1-yl)cinnoline-3-carboxylate | 489 | ethyl 6-bromo-4-[(3-chloro-2-fluoro-phenyl)amino]-7-ethoxy-cinnoline-3-carboxylate (Method 35) |
| 51 | Ethyl 7-ethoxy-4-[(2-fluoro-4-methyl-phenyl)amino]-6-(4-methylpiperazin-1-yl)cinnoline-3-carboxylate | 469 | ethyl 6-bromo-7-ethoxy-4-[(2-fluoro-4-methyl-phenyl)amino]cinnoline-3-carboxylate (Method 36) |
| 52 | Ethyl 4-[(2,4-difluorophenyl)amino]-7-ethoxy-6-(4-propan-2-ylpiperazin-1-yl)cinnoline-3-carboxylate | 501 | ethyl 6-bromo-4-[(2,4-difluorophenyl)amino]-7-ethoxycinnoline-3-carboxylate (Method 33) |
| 53 | Ethyl 4-[(2,4-difluorophenyl)amino]-7-ethoxy-6-(4-ethylpiperazin-1-yl)cinnoline-3-carboxylate | 486 | ethyl 6-bromo-4-[(2,4-difluorophenyl)amino]-7-ethoxycinnoline-3-carboxylate (Method 33) |
| 54 | 4-[(3-Chloro-2-fluorophenyl)amino]-7-methoxy-6-(4-methylpiperazin-1-yl)cinnoline-3-carbonitrile | 428 | 6-bromo-4-[(3-chloro-2-fluorophenyl)amino]-7-methoxycinnoline-3-carbonitrile Method 37 |
| 55 | 4-[(2-Fluoro-4-methylphenyl)amino]-6-(4-isopropylpiperazin-1-yl)-7-methoxycinnoline-3-carbonitrile | 435 | 6-bromo-4-[(2-fluoro-4-methylphenyl)amino]-7-methoxycinnoline-3-carbonitrile Method 38 |
| 56 | 6-(4-tert-Butylpiperazin-1-yl)-4-[(2-fluoro-4-methylphenyl)amino]-7-methoxycinnoline-3-carbonitrile | 449 | 6-bromo-4-[(2-fluoro-4-methylphenyl)amino]-7-methoxycinnoline-3-carbonitrile Method 38 |
| 57 | 4-[(2,4-Difluorophenyl)amino]-7-methoxy-6-(4-methylpiperazin-1-yl)cinnoline-3-carbonitrile | 411 | 6-bromo-4-[(2,4-difluorophenyl)amino]-7-methoxycinnoline-3-carbonitrile Method 39 |
| 58 | 4-[(2-Fluoro-5-methylphenyl)amino]-7-methoxy-6-(4-methylpiperazin-1-yl)cinnoline-3-carbonitrile | 407 | 6-bromo-4-[(2-fluoro-5-methylphenyl)amino]-7-methoxycinnoline-3-carbonitrile Method 40 |
| 59 | 4-[(2-Fluoro-5-methylphenyl)amino]-6-(4-isopropylpiperazin-1-yl)-7-methoxycinnoline-3-carbonitrile | 435 | 6-bromo-4-[(2-fluoro-5-methylphenyl)amino]-7-methoxycinnoline-3-carbonitrile Method 40 |
| 60 | 4-[(2-Fluoro-4-methylphenyl)amino]-7-methoxy-6-(4-methylpiperazin-1-yl)cinnoline-3-carbonitrile | 407 | 6-bromo-4-[(2-fluoro-4-methylphenyl)amino]-7-methoxycinnoline-3-carbonitrile Method 38 |
| 61 | 4-[(2,4-Difluorophenyl)amino]-7-(2-methoxyethoxy)-6-(4-methylpiperazin-1-yl)cinnoline-3-carbonitrile | 456 | 6-bromo-4-[(2,4-difluorophenyl)amino]-7-(2-methoxyethoxy)cinnoline-3-carbonitrile Method 41 |
| 62 | 4-[(2-Fluoro-4-methylphenyl)amino]-7-(2-methoxyethoxy)-6-(4-methylpiperazin-1-yl)cinnoline-3-carbonitrile | 451 | 6-bromo-4-[(2-fluoro-4-methylphenyl)amino]-7-(2-methoxyethoxy)cinnoline-3-carbonitrile Method 42 |
| 63 | 4-[(2-Fluoro-5-methylphenyl)amino]-7-(2-methoxyethoxy)-6-(4-methylpiperazin-1-yl)cinnoline-3-carbonitrile | 451 | 6-bromo-4-[(2-fluoro-5-methylphenyl)amino]-7-(2-methoxyethoxy)cinnoline-3-carbonitrile Method 43 |

-continued

| Method | Compound | m/z | Starting Material |
|---|---|---|---|
| 64 | 4-[(3-Chloro-2-fluorophenyl)amino]-7-(2-methoxyethoxy)-6-(4-methylpiperazin-1-yl)cinnoline-3-carbonitrile | 472 | 6-bromo-4-[(3-chloro-2-fluorophenyl)amino]-7-(2-methoxyethoxy)cinnoline-3-carbonitrile<br>Method 44 |
| 65 | 4-[(2,4-Difluorophenyl)amino]-6-(4-isopropylpiperazin-1-yl)-7-(2-methoxyethoxy)cinnoline-3-carbonitrile | 483 | 6-bromo-4-[(2,4-difluorophenyl)amino]-7-(2-methoxyethoxy)cinnoline-3-carbonitrile<br>Method 41 |
| 66 | 7-Ethoxy-4-[(2-fluoro-4-methylphenyl)amino]-6-(4-isopropylpiperazin-1-yl)cinnoline-3-carbonitrile | 449 | 6-bromo-7-ethoxy-4-[(2-fluoro-4-methylphenyl)amino]cinnoline-3-carbonitrile<br>Method 45 |
| 67 | 7-Ethoxy-4-[(2-fluoro-4-methylphenyl)amino]-6-(4-methyl-1,4-diazepan-1-yl)cinnoline-3-carbonitrile | 435 | 6-bromo-7-ethoxy-4-[(2-fluoro-4-methylphenyl)amino]cinnoline-3-carbonitrile<br>Method 45 |
| 68 | 6-[(3R,5S)-3,5-Dimethylpiperazin-1-yl]-7-ethoxy-4-[(2-fluoro-4-methylphenyl)amino]cinnoline-3-carbonitrile | 435 | 6-bromo-7-ethoxy-4-[(2-fluoro-4-methylphenyl)amino]cinnoline-3-carbonitrile<br>Method 45 |
| 69 | 4-[(2-Fluoro-4-methylphenyl)amino]-7-methoxy-6-[4-(2-methoxyethyl)piperazin-1-yl]cinnoline-3-carbonitrile | 451 | 6-bromo-4-[(2-fluoro-4-methylphenyl)amino]-7-methoxycinnoline-3-carbonitrile<br>Method 38 |
| 70 | 6-(5,6-Dihydro[1,2,4]triazolo[4,3-a]pyrazin-7(8H)-yl)-4-[(2-fluoro-4-methylphenyl)amino]-7-methoxycinnoline-3-carbonitrile | 431 | 6-bromo-4-[(2-fluoro-4-methylphenyl)amino]-7-methoxycinnoline-3-carbonitrile<br>Method 38 |
| 71 | 4-[(2-Fluoro-4-methylphenyl)amino]-6-(hexahydropyrrolo[1,2-a]pyrazin-2(1H)-yl)-7-methoxycinnoline-3-carbonitrile | 433 | 6-bromo-4-[(2-fluoro-4-methylphenyl)amino]-7-methoxycinnoline-3-carbonitrile<br>Method 38 |
| 72 | 4-[(2-Fluoro-4-methylphenyl)amino]-7-methoxy-6-morpholin-4-ylcinnoline-3-carbonitrile | 394 | 6-bromo-4-[(2-fluoro-4-methylphenyl)amino]-7-methoxycinnoline-3-carbonitrile<br>Method 38 |
| 73 | 6-[(3R,5S)-3,5-Dimethylpiperazin-1-yl]-4-[(2-fluoro-4-methylphenyl)amino]-7-methoxycinnoline-3-carbonitrile | 421 | 6-bromo-4-[(2-fluoro-4-methylphenyl)amino]-7-methoxycinnoline-3-carbonitrile<br>Method 38 |
| 74 | 6-[(2R,6S)-2,6-Dimethylmorpholin-4-yl]-4-[(2-fluoro-4-methylphenyl)amino]-7-methoxycinnoline-3-carbonitrile | 422 | 6-bromo-4-[(2-fluoro-4-methylphenyl)amino]-7-methoxycinnoline-3-carbonitrile<br>Method 38 |
| 75 | 6-[4-(2-{[tert-Butyl(dimethyl)silyl]oxy}ethyl)piperazin-1-yl]-4-[(2-fluoro-4-methylphenyl)amino]-7-methoxycinnoline-3-carbonitrile | 551 | 6-bromo-4-[(2-fluoro-4-methylphenyl)amino]-7-methoxycinnoline-3-carbonitrile<br>Method 38<br>and<br>1-(2-{[tert-butyl(dimethyl)silyl]oxy}ethyl)piperazine<br>Method 89 |
| 76 | 6-[4-(Dimethylamino)piperidin-1-yl]-4-[(2-fluoro-4-methylphenyl)amino]-7-methoxycinnoline-3-carbonitrile | 435 | 6-bromo-4-[(2-fluoro-4-methylphenyl)amino]-7-methoxycinnoline-3-carbonitrile<br>Method 38 |
| 77 | 4-[(2-Fluoro-4-methylphenyl)amino]-7-methoxy-6-(4-methyl-1,4-diazepan-1-yl)cinnoline-3-carbonitrile | 421 | 6-bromo-4-[(2-fluoro-4-methylphenyl)amino]-7-methoxycinnoline-3-carbonitrile<br>Method 38 |
| 78 | 6-[(3S)-3-(Dimethylamino)pyrrolidin-1-yl]-4-[(2-fluoro-4-methylphenyl)amino]-7-methoxycinnoline-3-carbonitrile | 421 | 6-bromo-4-[(2-fluoro-4-methylphenyl)amino]-7-methoxycinnoline-3-carbonitrile<br>Method 38 |
| 79 | 4-[(2-Fluoro-4-methylphenyl)amino]-7-methoxy-6-[4-(2,2,2-trifluoroethyl)piperazin-1-yl]cinnoline-3-carbonitrile | 475 | 6-bromo-4-[(2-fluoro-4-methylphenyl)amino]-7-methoxycinnoline-3-carbonitrile<br>Method 38 |

-continued

| Method | Compound | m/z | Starting Material |
|---|---|---|---|
| 80 | 6-[4-(2-{[tert-Butyl(dimethyl)silyl]oxy}ethyl)piperazin-1-yl]-7-ethoxy-4-[(2-fluoro-4-methylphenyl)amino]cinnoline-3-carbonitrile | 565 | 6-bromo-7-ethoxy-4-[(2-fluoro-4-methylphenyl)amino]cinnoline-3-carbonitrile Method 45 and 1-(2-{[tert-butyl(dimethyl)silyl]oxy}ethyl)piperazine Method 89 |
| 81 | 4-[(2,4-Difluorophenyl)amino]-6-[(3R,5S)-3,5-dimethylpiperazin-1-yl]-7-methoxycinnoline-3-carbonitrile | 425 | 6-bromo-4-[(2,4-difluorophenyl)amino]-7-methoxycinnoline-3-carbonitrile Method 39 |
| 82 | 4-[(3-Chloro-2-fluorophenyl)amino]-6-[(3R,5S)-3,5-dimethylpiperazin-1-yl]-7-methoxycinnoline-3-carbonitrile | 441 | 6-bromo-4-[(3-chloro-2-fluorophenyl)amino]-7-methoxycinnoline-3-carbonitrile Method 37 |
| 83 | 4-[(2-Fluoro-4-methylphenyl)amino]-7-methoxy-6-piperazin-1-ylcinnoline-3-carbonitrile | 393 | 6-bromo-4-[(2-fluoro-4-methylphenyl)amino]-7-methoxycinnoline-3-carbonitrile Method 38 |

Method 84

4-[(2-Fluoro-4-methylphenyl)amino]-7-methoxy-6-pyridin-4-ylcinnoline-3-carbonitrile To a mixture of 6-bromo-4-(2-fluoro-4-methylphenylamino)-7-methoxycinnoline-3-carbonitrile (Method 38, 0.25 g, 0.65 mmol), pyridin-4-ylboronic acid (0.159 g, 1.29 mmol) and $K_2CO_3$ (0.357 g, 2.58 mmol) in DMA (3.0 ml) and water (0.30 ml), was added $Pd(Ph_3P)_4$ (0.224 g, 0.19 mmol). The reaction was stirred under argon at 90° C. for 12 hours, cooled, diluted with water (50 mL) and extracted with EtOAc (2×50 mL). The combined organic extract was dried ($MgSO_4$), filtered, and the residue purified with silica chromatography (EtOAc) to give 0.175 g (64%) product. m/z 386.

Method 85

The following intermediate was prepared according to the procedure of Method 84 using the appropriate starting materials.

| Method | Compound | m/z | Starting Materials |
|---|---|---|---|
| 85 | tert-Butyl 4-{3-cyano-4-[(2-fluoro-4-methylphenyl)amino]-7-methoxycinnolin-6-yl}-3,6-dihydropyridine-1(2H)-carboxylate | 490 | 6-bromo-4-[(2-fluoro-4-methylphenyl)amino]-7-methoxycinnoline-3-carbonitrile Method 38 and tert-butyl 4-(4,4,5,5-tetramethyl-1,3,2-dioxaborolan-2-yl)-3,6-dihydropyridine-1(2H)-carboxylate |

Method 86

4-[(2-Fluoro-4-methylphenyl)amino]-6-(1-isopropyl-1,2,3,6-tetrahydropyridin-4-yl)-7-methoxycinnoline-3-carbonitrile To a solution of 4-(2-fluoro-4-methylphenylamino)-7-methoxy-6-(1,2,3,6-tetrahydropyridin-4-yl)cinnoline-3-carbonitrile (Method 88, 200 mg, 0.51 mmol) in dichloroethane (5 mL), acetone (0.566 mL, 7.70 mmol), and acetic acid (0.147 mL, 2.57 mmol) was added sodium triacetoxyborohydride (544 mg, 2.57 mmol) and the reaction stirred at 55° C. for 6 hours. The reaction mixture was concentrated under reduced pressure and the residue purified with silica chromatography (MeOH/EtOAc (1:1)) to give 120 mg (50%) product. m/z 432.

Method 87

The following intermediate was prepared according to the procedure of Method 86 using the appropriate starting materials.

| Method | Compound | m/z | Starting Material |
|---|---|---|---|
| 87 | 6-[1-(2-{[tert-Butyl(dimethyl)silyl]oxy}-ethyl)-1,2,3,6-tetrahydropyridin-4-yl]-4-[(2-fluoro-4-methylphenyl)amino]-7-methoxycinnoline-3-carbonitrile | 549 | 4-[(2-fluoro-4-methylphenyl)amino]-7-methoxy-6-(1,2,3,6-tetrahydropyridin-4-yl)cinnoline-3-carbonitrile Method 88 and (tert-butyldimethylsilyloxy)acetaldehyde |

Method 88

4-[(2-Fluoro-4-methylphenyl)amino]-7-methoxy-6-(1,2,3,6-tetrahydropyridin-4-yl)cinnoline-3-carbonitrile A solution of tert-butyl 4-(3-cyano-4-(2-fluoro-4-methylphenylamino)-7-methoxycinnolin-6-yl)-5,6-dihydropyridine-1(2H)-carboxylate (Method 85, 600 mg, 1.23 mmol) in $CH_2Cl_2$ (4.9 mL) and trifluoroacetic acid (4.9 mL, 63.6 mmol) was stirred for 2 hours. The reaction mixture was concentrated under reduced pressure, azeotroped with chloroform to remove trifluoroacetic acid, and the residue purified with reverse phase HPLC (MeCN/water) to give 302 mg (63%) product. m/z 390.

Method 89

1-(2-{[tert-Butyl(dimethyl)silyl]oxy}ethyl)piperazine

A mixture of benzyl 4-(2-(tert-butyldimethylsilyloxy)ethyl)piperazine-1-carboxylate (Method 90, 2.1 g, 5.55 mmol) and Pd/C (0.059 g, 0.55 mmol) in methanol (30 mL) was stirred under $H_2$ (g) for 24 hours. The reaction mixture was filtered through a pad of Celite and concentrated under reduced pressure to give 1.20 g, (88%) of a yellow oil. $^1H$ NMR: $CD_3Cl$ 3.74 (t, 2H), 2.90 (m, 4H), 2.51 (m, 6H), 0.88 (s, 9H), 0.04 (s, 6H).

Method 90

Benzyl 4-(2-{[tert-butyl(dimethyl)silyl]oxy}ethyl)piperazine-1-carboxylate

A mixture of benzyl 1-piperazinecarboxylate (1.751 mL, 9.08 mmol) and 2-(tert-butyldimethylsilyloxy)acetaldehyde (1.209 mL, 9.99 mmol), in MeOH (5 mL) and dichloroethane (5 mL) was stirred for 20 minutes with 4 Å molecular sieves. The mixture was added to a solution of sodium triacetoxyborohydride (4.81 g, 22.70 mmol) in tetrahydrofuran (5 mL) and stirred overnight. The reaction mixture was added to sodium bicarbonate (100 mL) and extracted with $CH_2Cl_2$ (3×50 mL). The combined organic extracts were concentrated under reduced pressure, and the residue purified with silica chromatography (EtOAc/MeOH) to give 2.10 g, (61%) of a clear oil. $^1H$ NMR: 7.34 (m, 5H), 5.05 (s, 2H), 3.67 (t, 2H), 3.36 (m, 4H), 2.40 (m, 6H), 0.84 (s, 9H), 0.02 (s, 6H).

The invention claimed is:

1. A compound of formula (I):

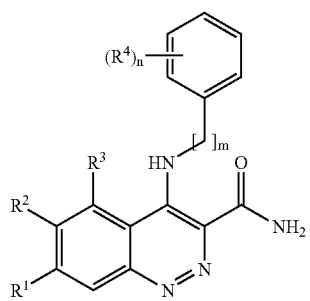

(I)

wherein:
- $R^1$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$carbamoyl, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^5$; and wherein if said heterocyclyl contains an —NH— moiety that nitrogen may be optionally substituted by a group selected from $R^6$;
- $R^2$ is monocyclic heterocyclyl;
- $R^3$ is hydrogen or halo;
- m is 0 or 1;
- $R^4$ is selected from halo, nitro, cyano, hydroxy, trifluoromethoxy, trifluoromethyl, amino, carboxy, carbamoyl, mercapto, sulphamoyl, $C_{1-4}$alkyl, $C_{2-4}$alkenyl, $C_{2-4}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;
- n is 0-5; wherein the values of $R^4$ are the same or different;
- $R^5$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^9$— or heterocyclyl-$R^{10}$—; wherein $R^5$ may be optionally substituted on carbon by one or more $R^{11}$; and wherein if said heterocyclyl contains an —NH-moiety that nitrogen may be optionally substituted by a group selected from $R^{12}$;
- $R^6$ and $R^{12}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-16}$alkyl)carbamoyl, N,N—($C_{1-6}$alkyl)carbamoyl, benzyl, benzyloxycarbonyl, benzoyl and phenylsulphonyl; wherein $R^6$ and $R^{12}$ independently of each other may be optionally substituted on carbon by one or more $R^{13}$;
- $R^{13}$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^{14}$— or heterocyclyl-$R^{15}$—; wherein $R^{13}$ may be optionally substituted on carbon by one or more $R^{16}$; and wherein if said heterocyclyl contains an —NH— moiety that nitrogen may be optionally substituted by a group selected from $R^{17}$;
- $R^9$, $R^{10}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_s$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-6}$alkyl and s is 0-2;
- $R^{17}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl) carbamoyl, benzyl, benzyloxycarbonyl, benzoyl and phenylsulphonyl;
- $R^7$, $R^{11}$ and $R^{16}$ are independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

2. A compound of formula (IA):

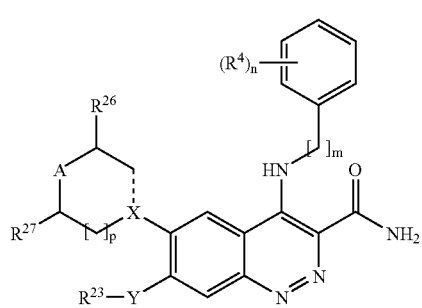

formula (IA)

or a pharmaceutically acceptable salt thereof, wherein:
- --- is selected from a single and double bond;
- if --- is a single bond, then X is selected from $CR^{24}$ and N;
- if --- is a double bond, then X is C;
- Y is selected from O and S;
- A is selected from O, S, $NR^{25}$, and $CR^{28}R^{29}$;
- p is 0-2;
- m is 0 or 1;
- $R^4$ is independently selected from halo, nitro, cyano, hydroxy, trifluoromethoxy, trifluoromethyl, amino, carboxy, carbamoyl, mercapto, sulphamoyl, $C_{1-4}$alkyl, $C_{2-4}$alkenyl, $C_{2-4}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;
- n is 0-5; wherein the values of $R^4$ are the same or different;
- $R^7$ may be independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;
- $R^{23}$ is selected from H, and $C_{1-6}$alkyl wherein $C_{1-6}$alkyl is optionally substituted with $C_{1-6}$alkoxy;
- $R^{24}$, $R^{26}$, $R^{27}$, $R^{28}$ are each independently selected from hydrogen and $C_{1-6}$alkyl;
- $R^{25}$ may be selected from hydrogen, $C_{1-6}$alkyl and $C_{1-6}$alkanoyl, wherein $C_{1-6}$alkyl and $C_{1-6}$alkanoyl may be optionally substituted on carbon by one or more $R^{30}$;
- or $R^{25}$ and $R^{27}$ together with the atom they are attached may optionally form a heterocyclic ring; wherein said heterocyclic ring may be optionally substituted on carbon by one or more $R^{35}$; and wherein if said heterocyclic ring contains an —NH— moiety that nitrogen may be optionally substituted by a group selected from $R^{36}$;
- $R^{29}$ may be selected from hydrogen and amino, wherein amino may be optionally substituted with one or more $C_{1-6}$alkyl;
- $R^{30}$ may be selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl;
- $R^{35}$ may be independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and
- $R^{36}$ may be selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl.

3. A compound of formula (IB):

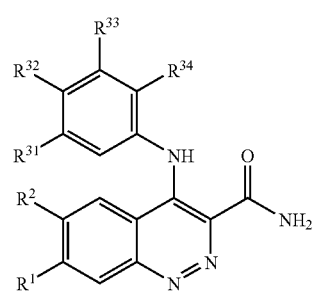

formula (IB)

or a pharmaceutically acceptable salt thereof, wherein:
- $R^1$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$-carbamoyl, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^5$; and wherein if said heterocyclyl contains an —NH— moiety that nitrogen may be optionally substituted by a group selected from $R^6$;

$R^2$ is monocyclic hetercyclyl;

$R^5$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^9$— or heterocyclyl-$R^{10}$—; wherein $R^5$ may be optionally substituted on carbon by one or more $R^{11}$; and wherein if said heterocyclyl contains an —NH-moiety that nitrogen may be optionally substituted by a group selected from $R^{12}$;

$R^6$ and $R^{12}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^6$ and $R^{12}$ independently of each other may be optionally substituted on carbon by one or more $R^{13}$;

$R^{13}$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, N—($C_{1-6}$alkyl)-N—($C_{1-6}$alkoxy)amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, carbocyclyl-$R^{14}$— or heterocyclyl-$R^{15}$—; wherein $R^{13}$ may be optionally substituted on carbon by one or more $R^{16}$; and wherein if said heterocyclyl contains an —NH— moiety that nitrogen may be optionally substituted by a group selected from $R^{17}$;

$R^9$, $R^{10}$, $R^{14}$ and $R^{15}$ are independently selected from a direct bond, —O—, —N($R^{18}$)—, —C(O)—, —N($R^{19}$)C(O)—, —C(O)N($R^{20}$)—, —S(O)$_s$—, —SO$_2$N($R^{21}$)— or —N($R^{22}$)SO$_2$—; wherein $R^{18}$, $R^{19}$, $R^{20}$, $R^{21}$ and $R^{22}$ are independently selected from hydrogen or $C_{1-6}$alkyl and s is 0-2;

$R^{17}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

$R^{11}$ and $R^{16}$ are independently selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{31}$, $R^{32}$, $R^{33}$, and $R^{34}$ are each independently selected from hydrogen, halo, and $C_{1-4}$alkyl.

4. A compound of formula (IC):

formula (IC)

or a pharmaceutically acceptable salt thereof, wherein:

--- is selected from a single and double bond;

if --- is a single bond, then X is selected from $CR^{24}$ and N;

if --- is a double bond, then X is C;

Y is selected from O and S;

A is selected from O, S, $NR^{25}$, and $CR^{28}R^{29}$;

p is 0-2;

$R^{23}$ is $C_{1-6}$alkyl;

$R^{24}$, $R^{26}$, $R^{27}$, $R^{28}$ are each independently selected from hydrogen and $C_{1-6}$alkyl;

$R^{25}$ may be selected from hydrogen, $C_{1-6}$alkyl and $C_{1-6}$alkanoyl wherein $C_{1-6}$alkyl and $C_{1-6}$alkanoyl may be optionally substituted on carbon by one or more $R^{30}$;

$R^{29}$ may be selected from hydrogen and amino optionally substituted with one or more $C_{1-6}$alkyl;

$R^{30}$ may be selected from halo, nitro, cyano, hydroxy, trifluoromethoxy, trifluoromethyl, amino, carboxy, carbamoyl, mercapto, sulphamoyl, $C_{1-6}$alkyl, $C_{2-6}$alkenyl, $C_{2-6}$alkynyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, phenyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, and N-methyl-N-ethylsulphamoyl;

$R^{31}$ is selected from hydrogen and $C_{1-4}$alkyl;

$R^{32}$ is selected from hydrogen, halo, and $C_{1-4}$alkyl;

$R^{33}$ is selected from hydrogen and halo; and $R^{34}$ is selected from halo.

5. A compound of formula (ID):

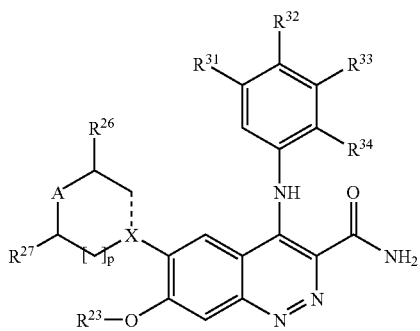

formula (ID)

or a pharmaceutically acceptable salt thereof, wherein:
--- is selected from a single and double bond;
if --- is a single bond, then X is selected from CH and N;
if --- is a double bond, then X is C;
A is selected from O, $NR^{25}$, and $CHR^{29}$;
p is 0-2;
$R^{23}$ is selected from methyl and ethyl;
$R^{25}$ is selected from hydrogen, methyl, ethyl, isopropyl, tert-butyl, 1-methoxy-2-ethyl, 1-hydroxy-2-ethyl, 1,1,1-trifluoro-2-ethyl, 2-hydroxy-1-propionyl, and mesyl;
$R^{26}$ and $R^{27}$ are each independently selected from hydrogen and methyl;
$R^{29}$ may be dimethylamino;
$R^{31}$ is selected from hydrogen and methyl;
$R^{32}$ is selected from hydrogen, fluoro, and methyl;
$R^{33}$ is selected from hydrogen and chloro; and
$R^{34}$ is selected from fluoro and chloro.

6. A compound of formula (I) or a pharmaceutically acceptable salt thereof selected from:
7-Ethoxy-4-[(2-fluoro-4-methyl-phenyl)amino]-6-(4-methylpiperazin-1-yl)cinnoline-3-carboxamide;
4-(2-Fluoro-4-methylphenylamino)-7-methoxy-6-(4-methylpiperazin-1-yl)cinnoline-3-carboxamide;
4-[(2,4-Difluorophenyl)amino]-7-methoxy-6-(4-methylpiperazin-1-yl)cinnoline-3-carboxamide;
6-[(3R,5S)-3,5-Dimethylpiperazin-1-yl]-4-[(2-fluoro-4-methylphenyl)amino]-7-methoxycinnoline-3-carboxamide;
4-[(2-Fluoro-4-methylphenyl)amino]-6-[4-(2-hydroxyethyl)piperazin-1-yl]-7-methoxycinnoline-3-carboxamide;
7-Ethoxy-4-[(2-fluoro-4-methylphenyl)amino]-6-[4-(2-hydroxyethyl)piperazin-1-yl]cinnoline-3-carboxamide;
4-[(3-Chloro-2-fluorophenyl)amino]-6-[(3R,5S)-3,5-dimethylpiperazin-1-yl]-7-methoxycinnoline-3-carboxamide;
4-[(2-Fluoro-4-methylphenyl)amino]-6-(1-isopropylpiperidin-4-yl)-7-methoxycinnoline-3-carboxamide hydrochloride;
4-[(2-Fluoro-4-methylphenyl)amino]-6-[1-(2-hydroxyethyl)piperidin-4-yl]-7-methoxycinnoline-3-carboxamide; and
4-[(2-Fluoro-4-methylphenyl)amino]-6-{4-[(2R)-2-hydroxypropanoyl]piperazin-1-yl}-7-methoxycinnoline-3-carboxamide.

7. A process of producing a compound of formula (I), or a pharmaceutically acceptable salt thereof, as in claim 1 comprising hydrolyzing of a compound of formula (VI):

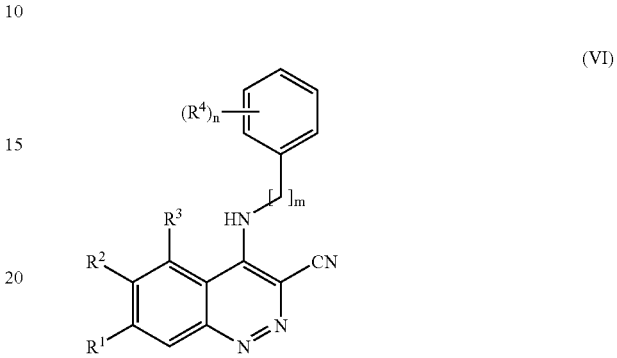

(VI)

such that a compound of formula (I) is formed;
and optionally thereafter:
i) converting a compound of the formula (I) into another compound of the formula (I);
ii) removing any protecting groups; or
iii) forming a pharmaceutically acceptable salt.

8. A process of producing a compound of formula (I), or a pharmaceutically acceptable salt thereof, as in claim 1, comprising reacting a compound of formula (VI),

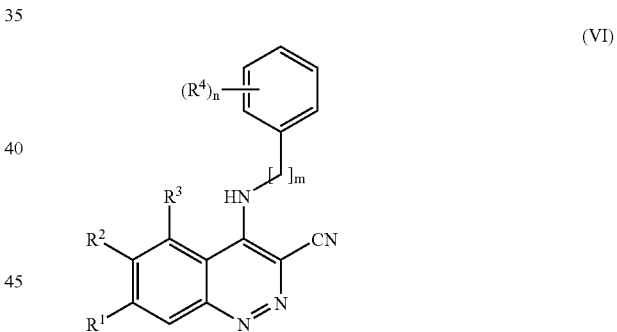

(VI)

with a metal hydroxide and a tertiary alcohol such that a compound of formula (I) is formed.

9. The process of claim 8, wherein said metal hydroxide is potassium hydroxide.

10. The process of claim 8, wherein said tertiary alcohol is tert-butyl alcohol.

11. The compound 4-[(2-fluoro-4-methylphenyl)amino]-6-[4-(2-hydroxyethyl)piperazin-1-yl]-7-methoxycinnoline-3-carboxamide, or a pharmaceutically salt thereof.

* * * * *